United States Patent
Riebel et al.

(10) Patent No.: US 8,330,046 B2
(45) Date of Patent: Dec. 11, 2012

(54) DEVICE FOR ANALYSIS OF A SAMPLE ON A TEST ELEMENT

(75) Inventors: Stefan Riebel, Cham (CH); Manfred Augstein, Mannheim (DE); Gregor Bainczyk, Mannheim (DE); Albert Grosser, Duesseldorf (DE); Oliver Kube, Worms (DE); Dieter Meinecke, Mannheim (DE); Bruno Thös, Quierschied (DE); Herbert Wieder, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1272 days.

(21) Appl. No.: 12/105,993

(22) Filed: Apr. 18, 2008

(65) Prior Publication Data

US 2008/0277280 A1 Nov. 13, 2008

Related U.S. Application Data

(63) Continuation of application No. PCT/EP2006/067709, filed on Oct. 24, 2006.

(30) Foreign Application Priority Data

Oct. 25, 2005 (EP) .................................... 05023219

(51) Int. Cl.
*H01B 5/14* (2006.01)
(52) U.S. Cl. ..................... 174/126.4; 174/250; 204/406; 204/297.1; 204/297.8
(58) Field of Classification Search .................. 204/406, 204/297.06–297.16; 174/126.4, 250–268
See application file for complete search history.

(56) References Cited

U.S. PATENT DOCUMENTS

| | | | |
|---|---|---|---|
| 4,654,197 A | 3/1987 | Lilja et al. | |
| 4,694,572 A * | 9/1987 | Leber et al. | 29/840 |
| 5,108,564 A | 4/1992 | Szuminsky et al. | |
| 5,220,488 A * | 6/1993 | Denes | 361/749 |
| 5,267,126 A * | 11/1993 | Henschen et al. | 361/826 |
| 5,424,035 A | 6/1995 | Hoenes et al. | |
| 5,575,403 A | 11/1996 | Charlton et al. | |
| 5,846,837 A | 12/1998 | Thym et al. | |
| 6,036,919 A | 3/2000 | Thym et al. | |
| 6,475,436 B1 | 11/2002 | Schabbach et al. | |
| 6,707,554 B1 | 3/2004 | Miltner et al. | |
| 6,784,376 B1 * | 8/2004 | Huemoeller et al. | 174/262 |
| 7,008,799 B1 | 3/2006 | Zimmer et al. | |
| 7,048,533 B2 | 5/2006 | Ils et al. | |
| 7,262,061 B2 | 8/2007 | Petrich et al. | |

(Continued)

FOREIGN PATENT DOCUMENTS

DE 19717882 C2 11/1998

(Continued)

OTHER PUBLICATIONS

Machine translation to English of DE 19717882 A1.*

(Continued)

*Primary Examiner* — J. Christopher Ball
(74) *Attorney, Agent, or Firm* — Krieg DeVault LLP

(57) ABSTRACT

An analysis device for analysis of a sample on a test element is provided that comprises at least one component configured to make electrical contact with at least one other component for electrical transmission therebetween. The at least one component generally comprises an injection-molded circuit mount, also called an MID, or molded interconnect device.

20 Claims, 18 Drawing Sheets

U.S. PATENT DOCUMENTS

| | | |
|---|---|---|
| 2002/0057993 A1 | 5/2002 | Maisey et al. |
| 2002/0076349 A1 | 6/2002 | Aitken et al. |
| 2004/0102060 A1 | 5/2004 | Schauz et al. |
| 2004/0178216 A1 | 9/2004 | Brickwood et al. |
| 2004/0190587 A1 | 9/2004 | Eisenschmid et al. |
| 2005/0135968 A1 | 6/2005 | Augstein |
| 2005/0141592 A1 | 6/2005 | Ocvirk et al. |
| 2005/0143675 A1 | 6/2005 | Neel et al. |

FOREIGN PATENT DOCUMENTS

| | | |
|---|---|---|
| DE | 19753847 A1 | 6/1999 |
| DE | 19854316 A1 | 10/1999 |
| DE | 19831394 B4 | 3/2000 |
| DE | 19902601 A1 | 7/2000 |
| DE | 102 55 325 A1 | 6/2004 |
| DE | 10359160 A1 | 7/2005 |
| EP | 0618443 A1 | 3/1994 |
| EP | 0732590 A2 | 1/1996 |
| EP | 0821233 A2 | 7/1997 |
| EP | 0821234 A2 | 7/1997 |
| EP | 0505475 B1 | 3/1999 |
| EP | 1457913 A2 | 7/1999 |
| EP | 1079379 A2 | 8/2000 |
| EP | 1 079 379 A2 | 2/2001 |
| EP | 1383360 A1 | 7/2002 |
| JP | 8262026 | 10/1996 |
| JP | 2001052371 | 2/2001 |
| JP | 2005186623 | 7/2005 |
| WO | WO 85/02257 | 5/1985 |
| WO | 97/02487 A1 | 1/1997 |
| WO | 00/19185 A1 | 4/2000 |
| WO | 00/67982 A1 | 11/2000 |
| WO | 01/48461 A1 | 7/2001 |

OTHER PUBLICATIONS

Frisch, David C., "Circuitry in Three Dimensions: Multifunctional Molded Plastic Packages", IEEE Transactions on Industry Applications, vol. 27, No. 3, May/Jun. 1991, pp. 442-446—XP-002374388.

Feldmann, K., et al., "New Requirements and Solutions for Product Data Processing of Three-Dimensional Molded Interconnection Devices", IEEE Int'l Electronics Manufacturing Technology Symposium, 1992, pp. 94-99.

Spanier, G., et al., "Biocompatible Assembling and Packaging Technology Demonstrated by the Integration of a Micro Sensor on a Micro Blood Pump", Proceeding of IEEE Sensors 2003, 2nd IEEE International Conference on Sensors, Toronto, Canada, Oct. 2003, vol. 2, Conf. 2, pp. 991-995.

Jung, Erik et al., "Packaging of an Electronic-Microfluidic Hybrid Sensor", Proceedings 53rd Electronic Components and Technology Conference, New Orleans, May 2003, Proceeding of the Electronic Components and Technology Conference, New York, vol. 53, May 2003, pp. 373-376.

Eisenbarth, M., et al., "Pressfit Technology for 3-D Molded Interconnect Devices (MID)—A lead-free Alternative to Solder Joints—Challenges and Solutions Concepts", IEEE/SEMI Technology Symposium: International Electronics Manufacturing Technology (IEMT) Symposium, 2002, pp. 238-244.

Penta Media: "Molded Interconnect Devices Reshape Electromechanical Design", Online, Sep. 2000, pp. 1-7. XP002374387.

Poehlau, Frank: "Raeumliche Schaltungstraeger—Rationalisieren durch Integration (3-Dimensional Circuit Carriers-Rationalization through Integration)", SIEMENS-WEBZINE, Online Nr. Jan. 1997, 2002, pp. 1-6. XP002374386.

Document entitled "Our Comments", discussing Japanese references, 2011, 5 pages.

* cited by examiner

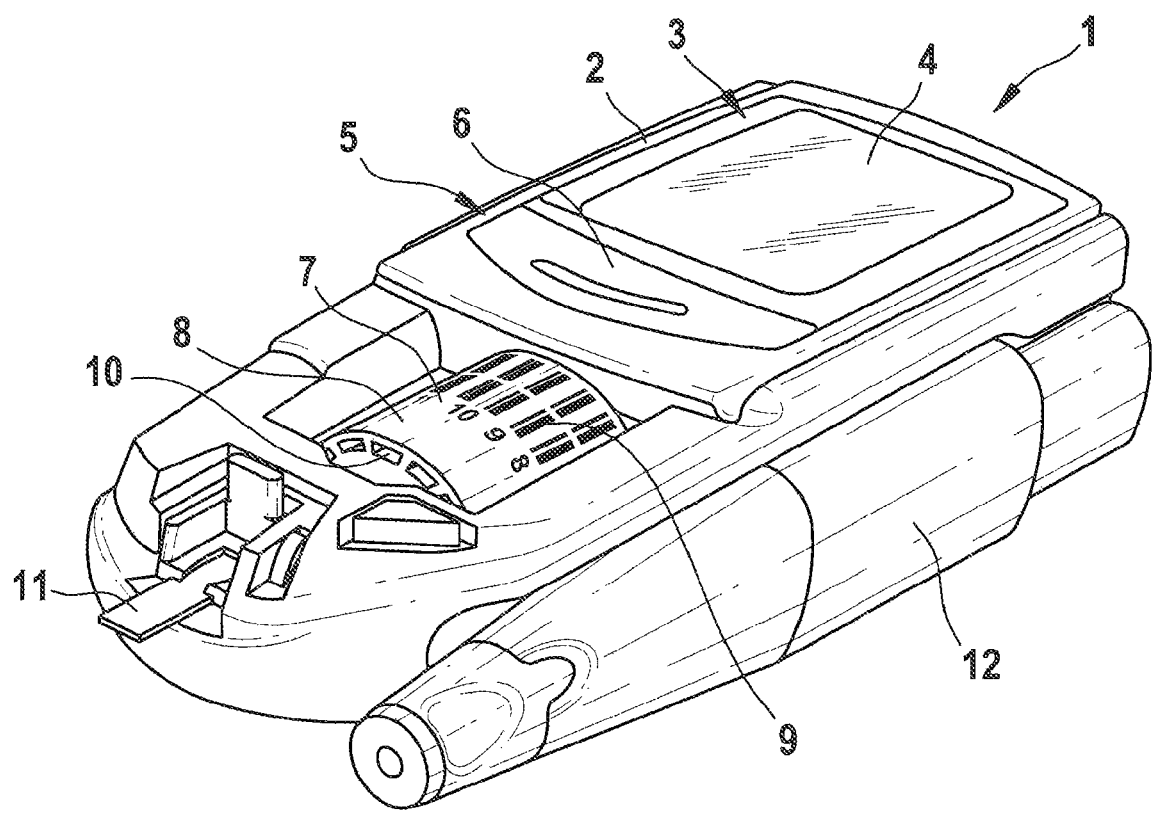
Fig. 1.1

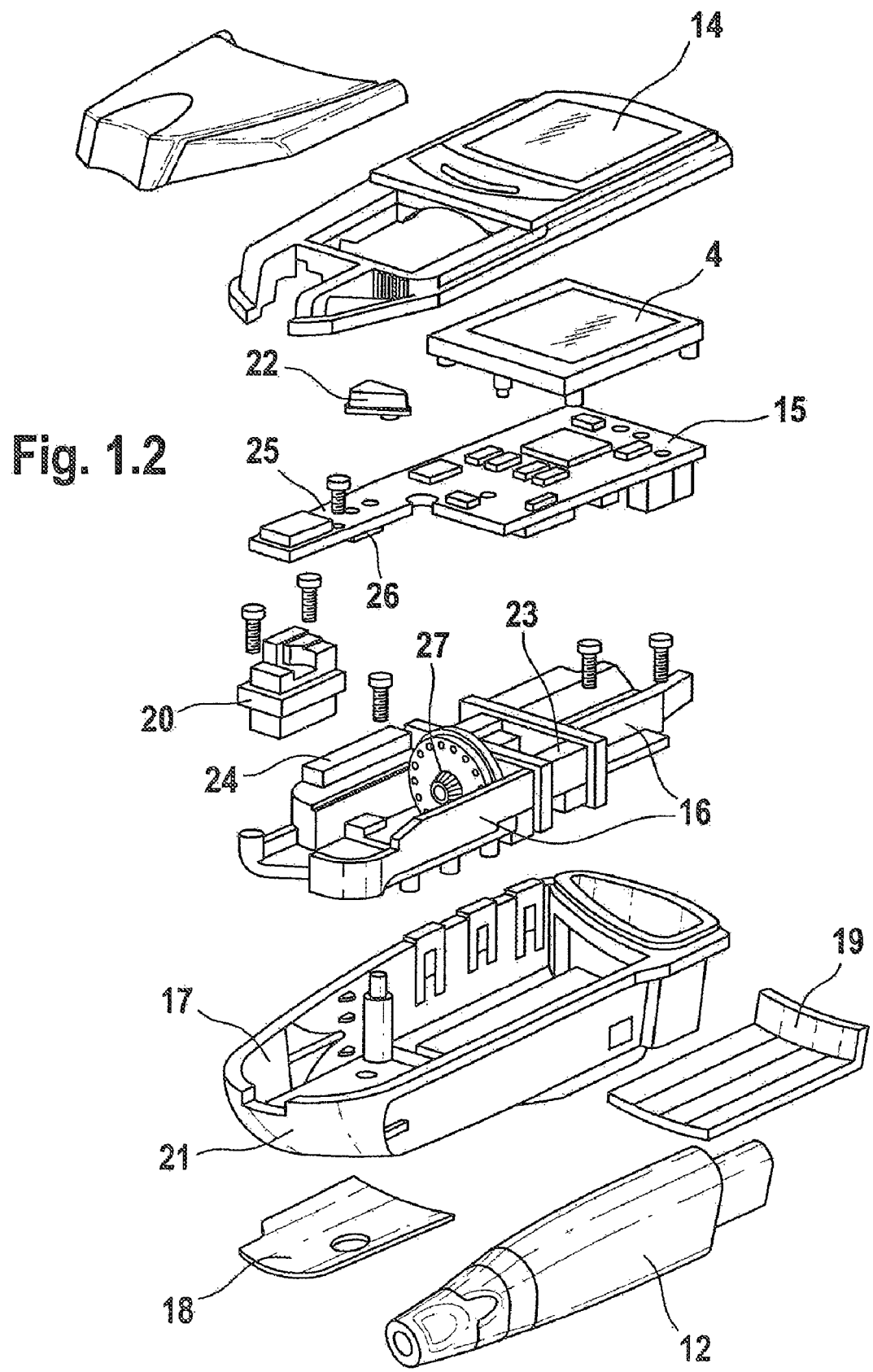
Fig. 1.2

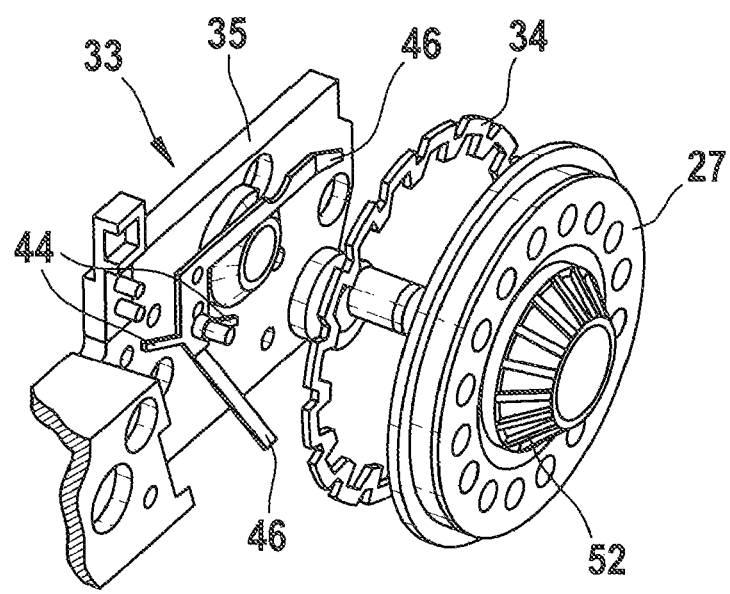
Fig. 3.1
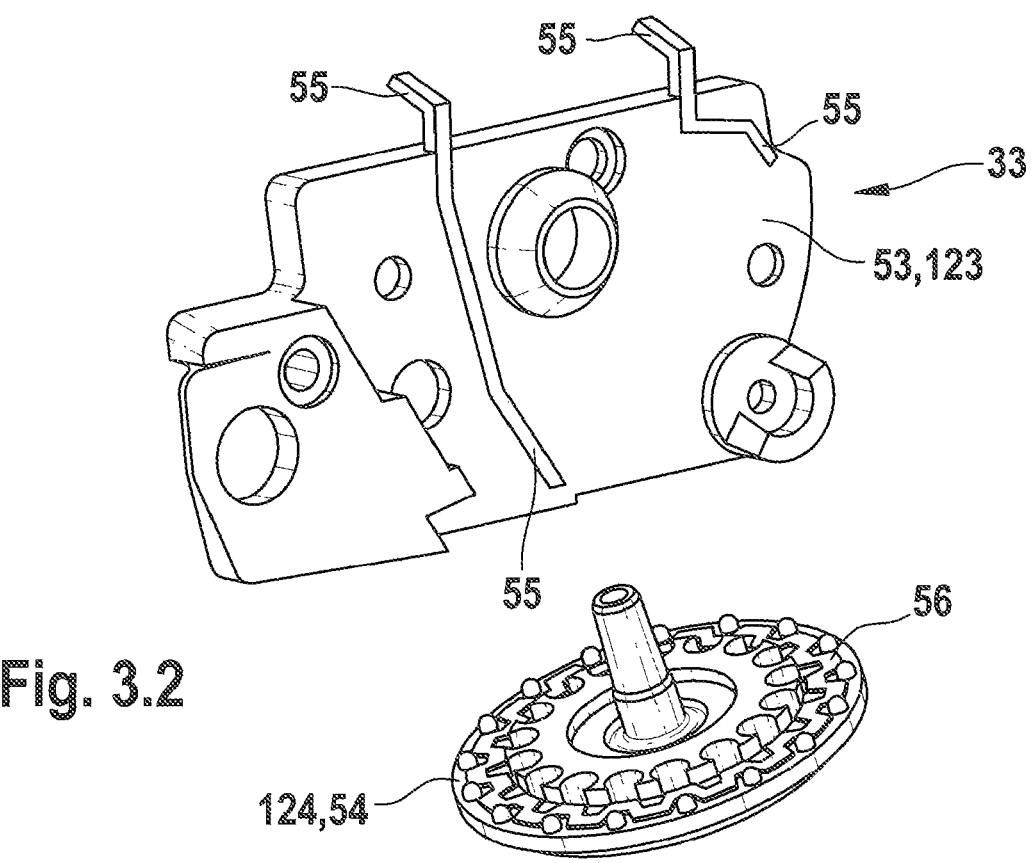
Fig. 3.2

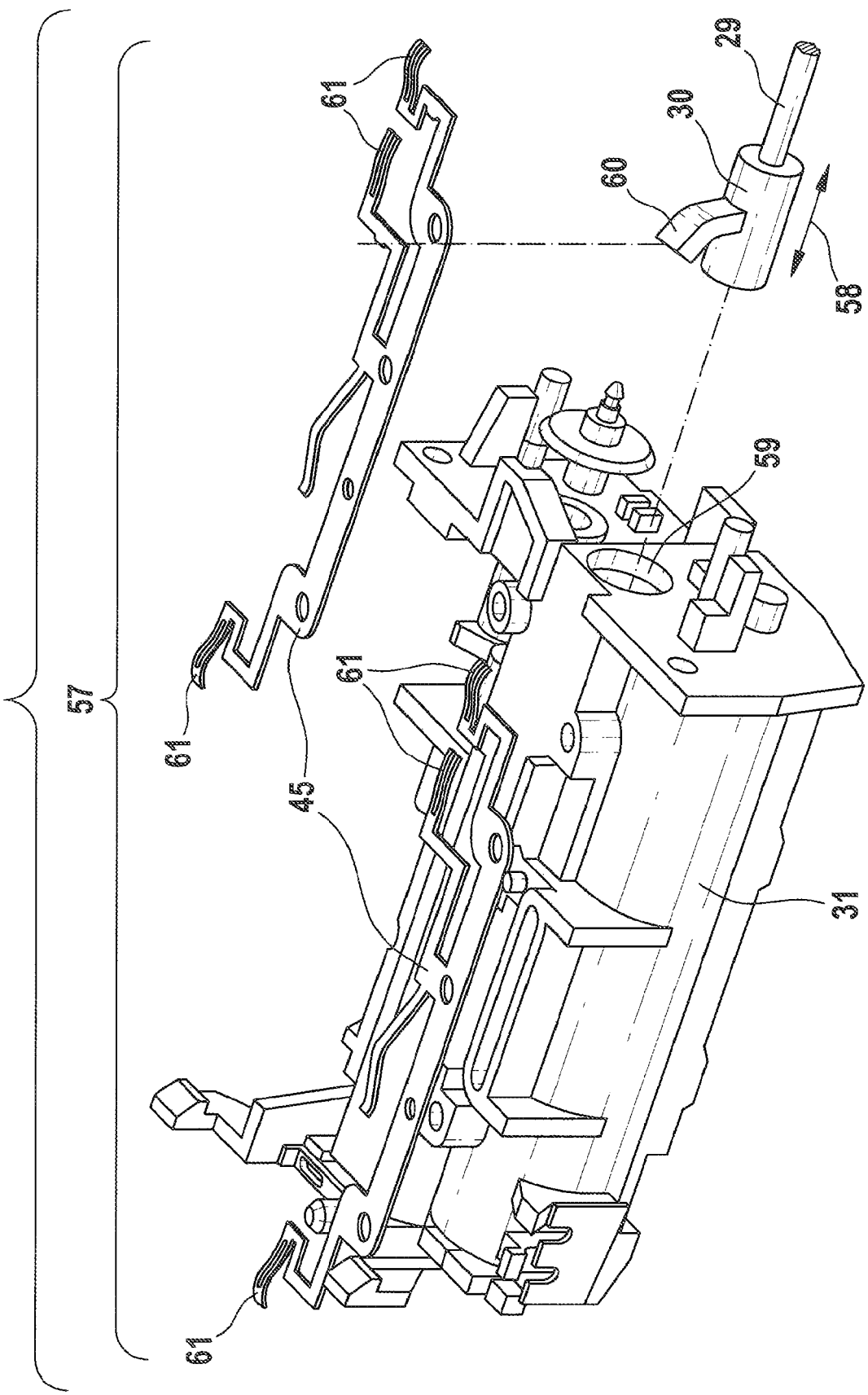

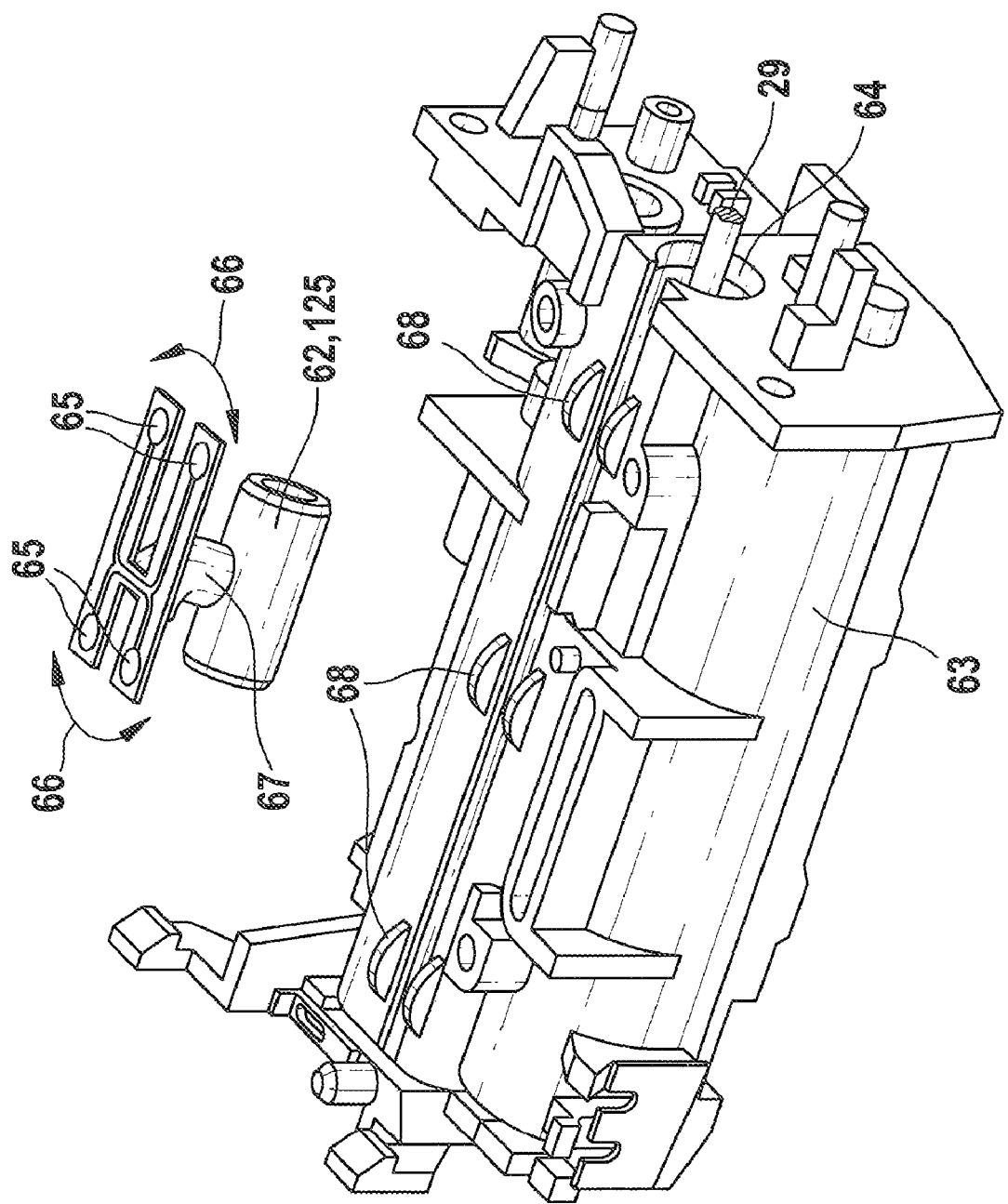

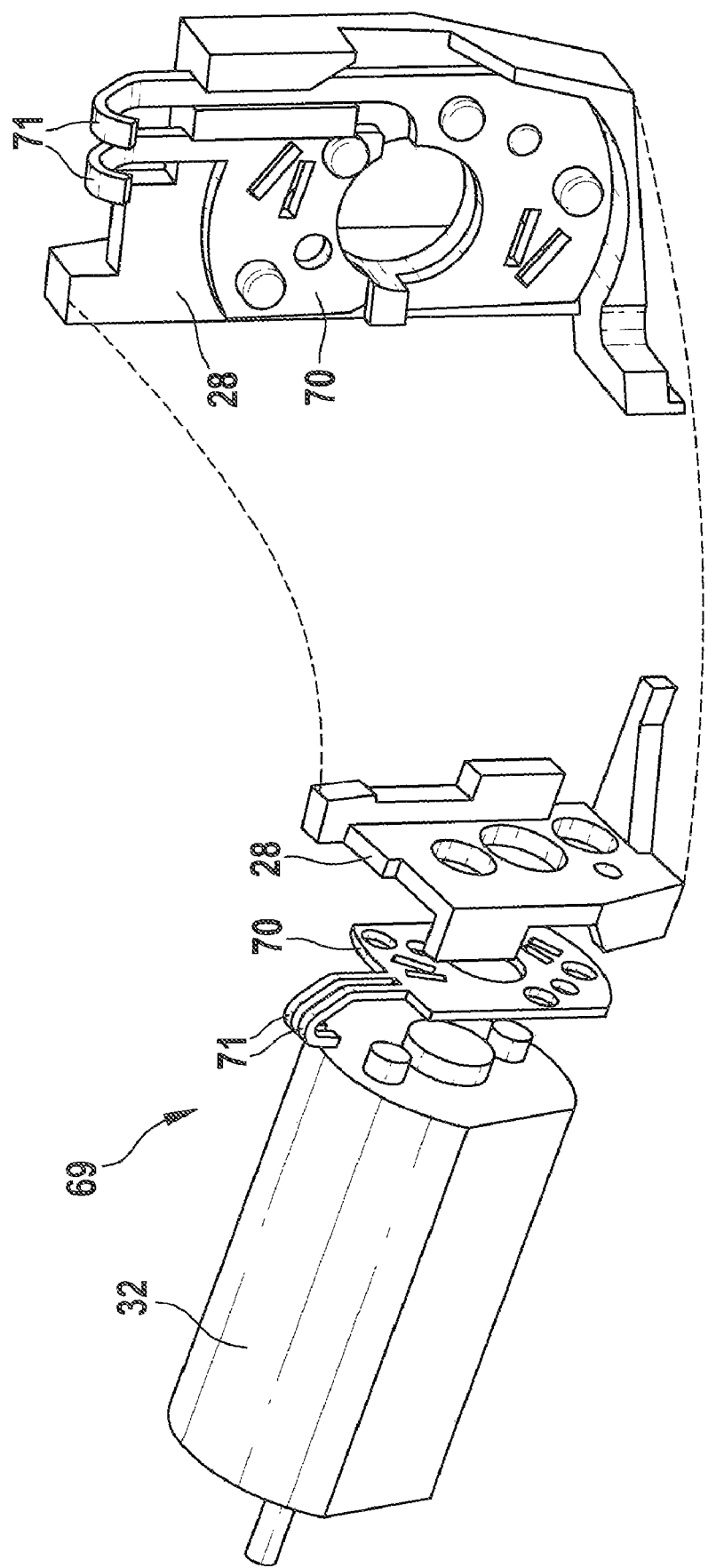

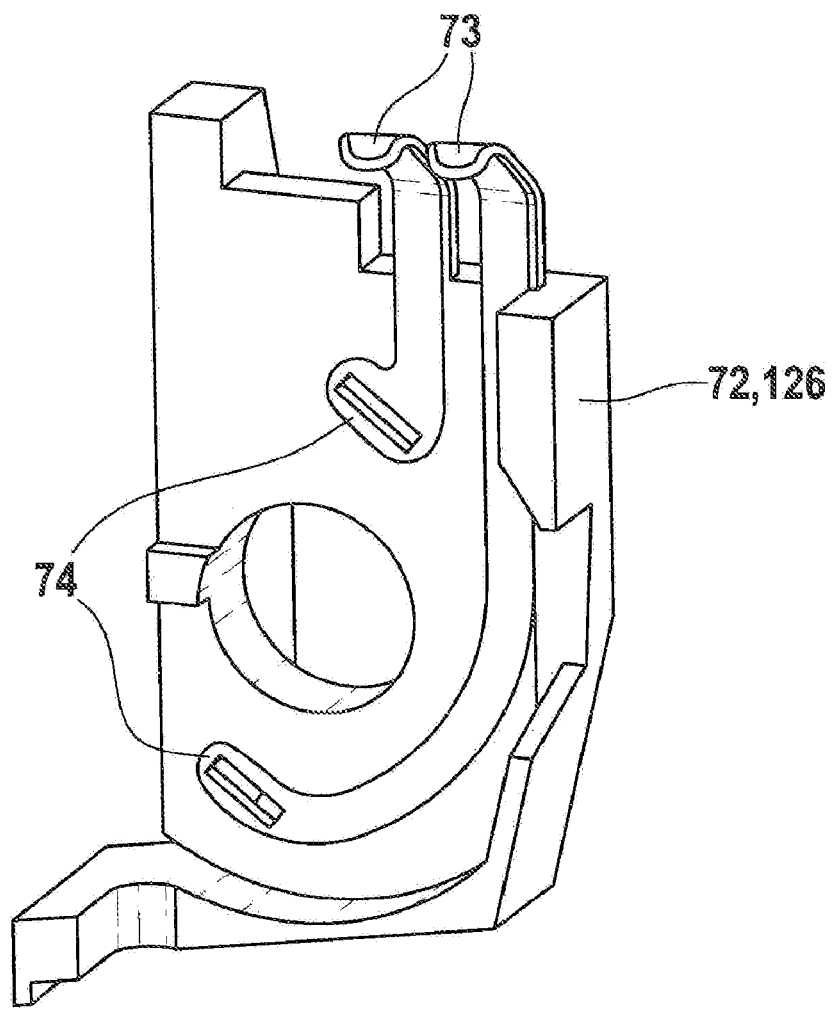
Fig. 5.2

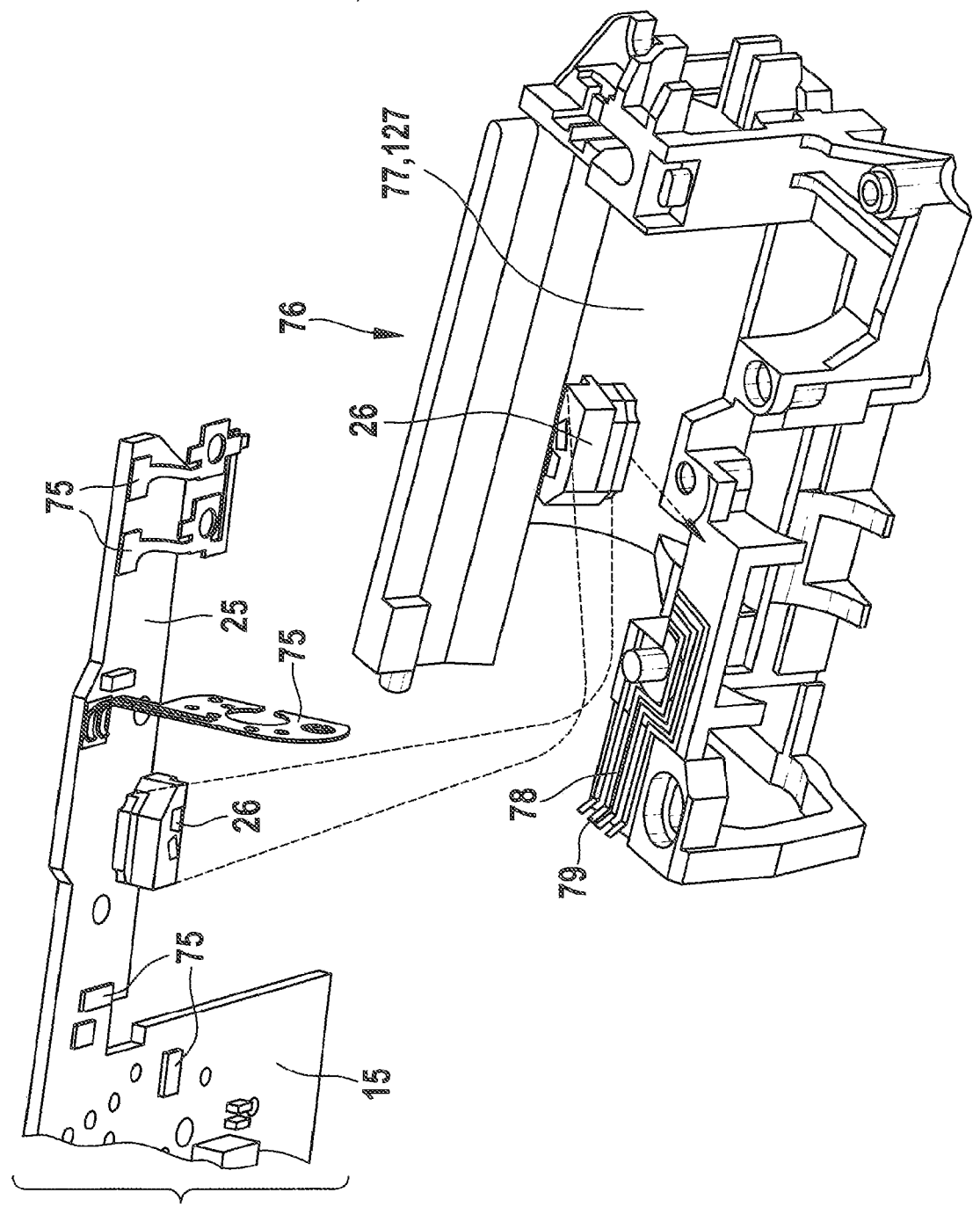

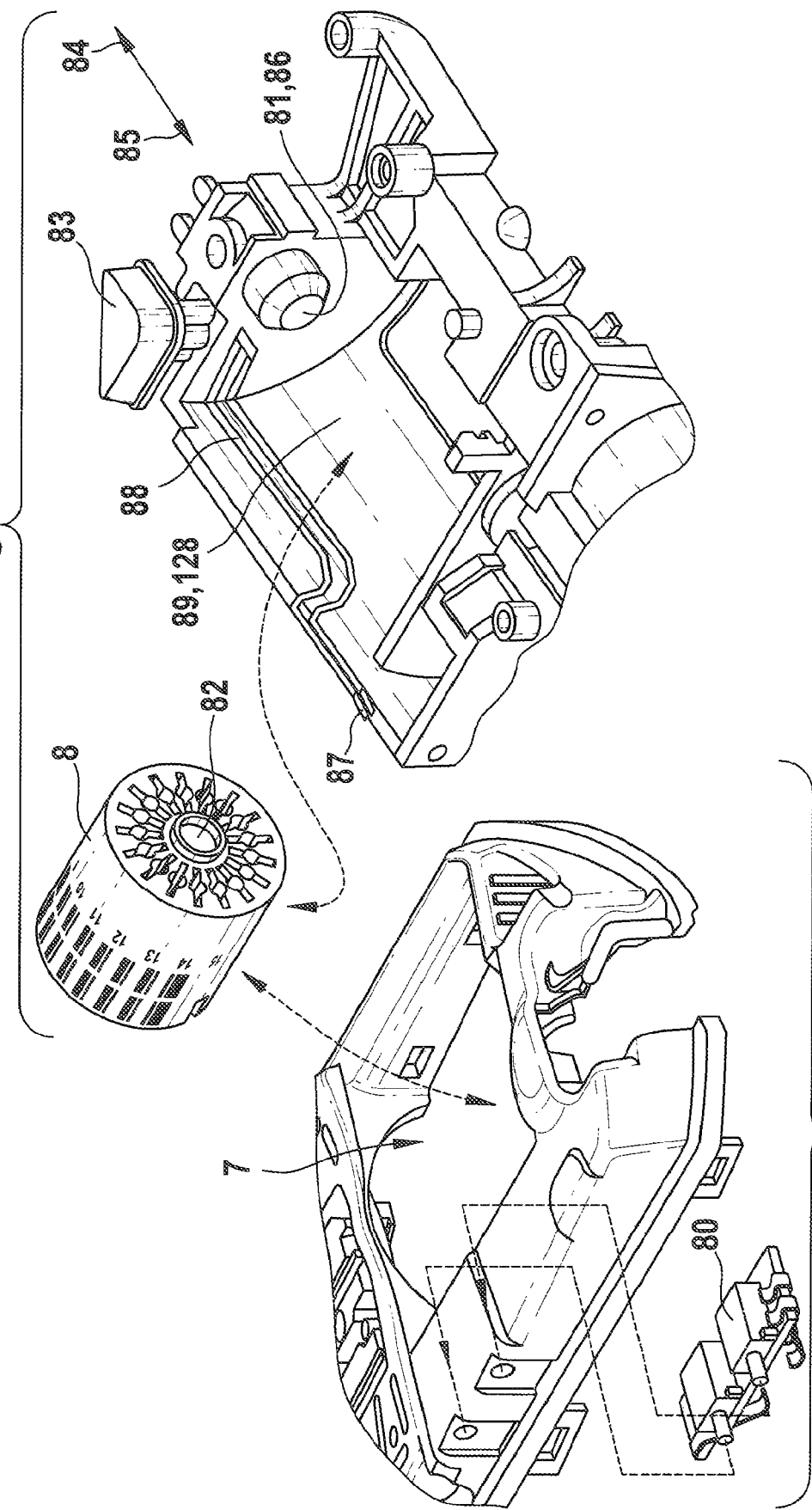

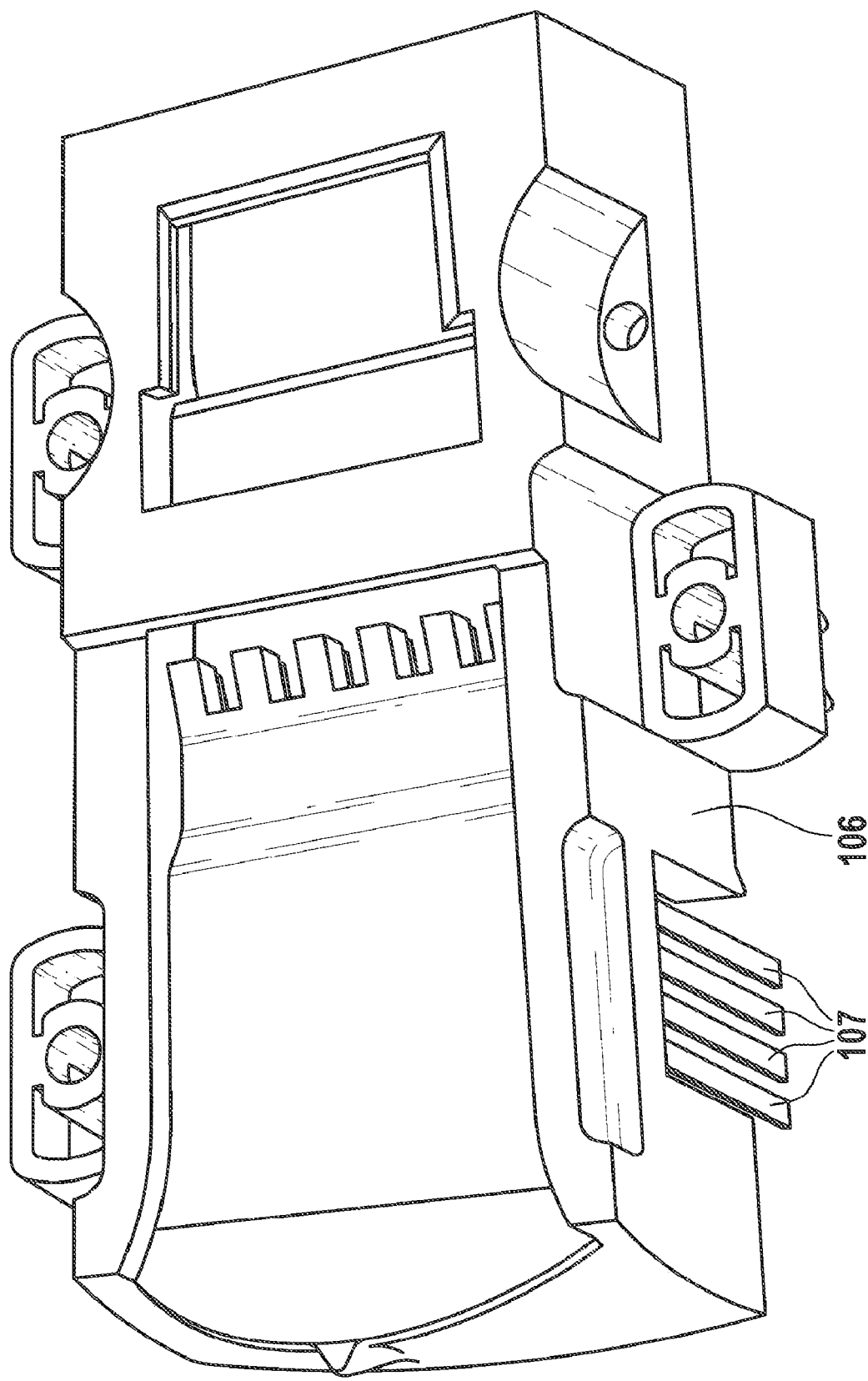

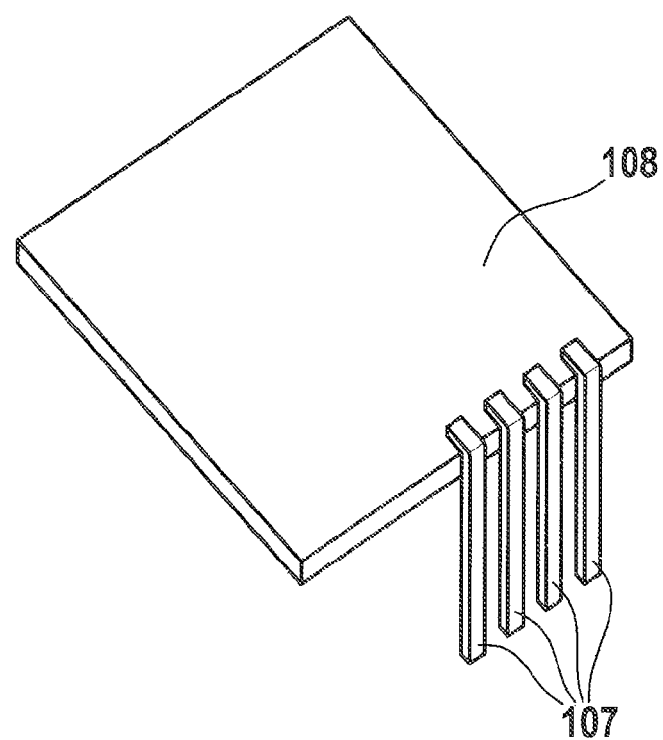
Fig. 11.2
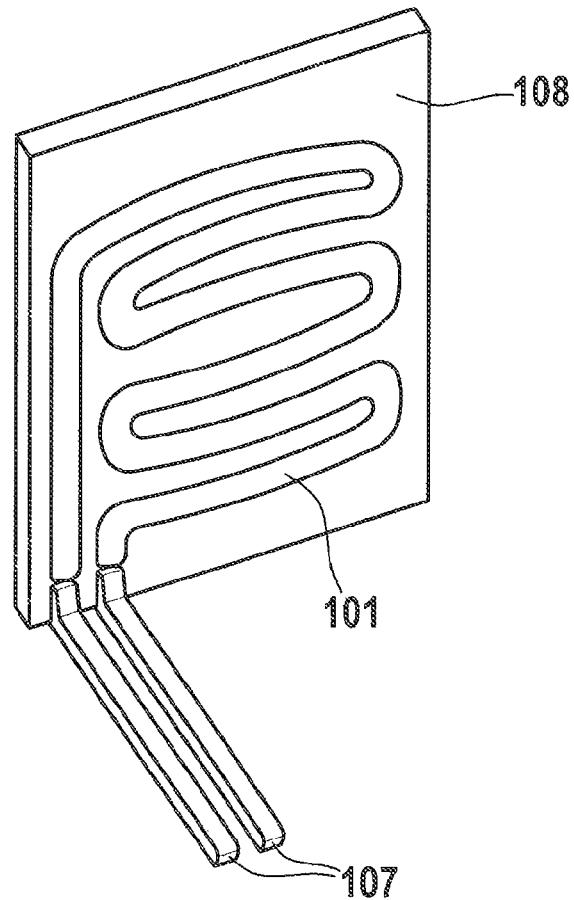
Fig. 11.3

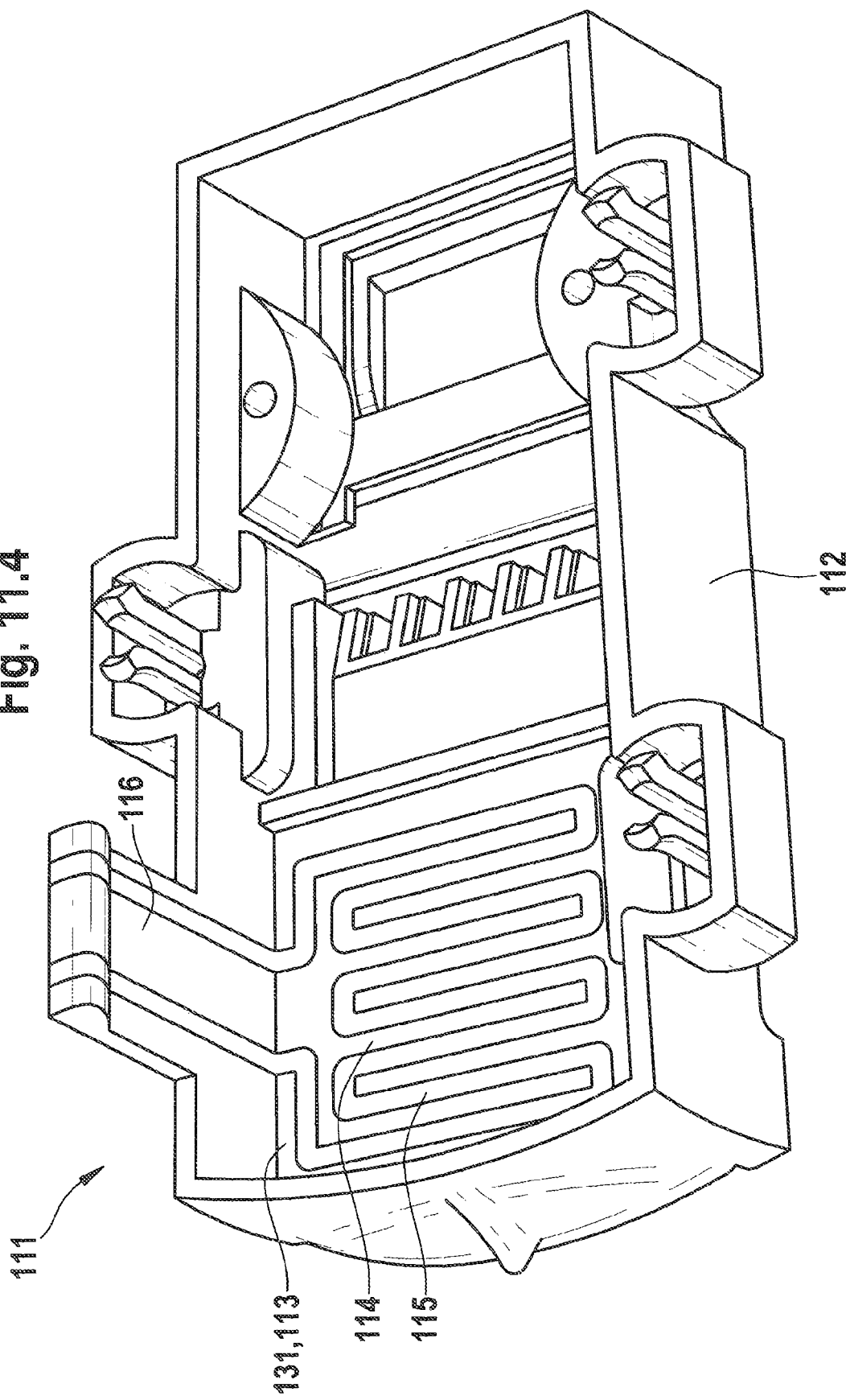
Fig. 11.4

DEVICE FOR ANALYSIS OF A SAMPLE ON A TEST ELEMENT

CLAIM OF PRIORITY

The present application is a continuation of and claims priority to PCT Application No. PCT/EP2006/067709, filed Oct. 24, 2006, which in turn claims the priority benefit of European Patent Application No. 05023219.8, filed Oct. 25, 2005, each of which are hereby incorporated by reference in their entireties.

TECHNICAL FIELD OF THE INVENTION

The present invention pertains to an analysis device for analysis of a sample on an analytical test element, which contains at least one component which makes electrical contact for transmission of electrical power, and in particular the present invention pertains to such devices in which the at least one component comprises an injection-molded circuit mount such as a molded interconnect device.

BACKGROUND

Samples, for example bodily fluids such as blood or urine, are frequently analyzed using analysis devices in which the samples to be analyzed are located on a test element and may react with one or more reagents on the test element in a test area before they are analyzed. The optical, in particular photometric evaluation, and the electrochemical evaluation of test elements represent the most usual methods for rapid determination of the concentration of analytes in samples. Analysis systems with test elements for sample analysis are generally used in the field of analysis, environmental analysis and in particular in the field of medical diagnosis. Particularly in the field of blood glucose diagnosis from capillary blood, test elements which are evaluated photometrically or electrochemically play a major role.

There are various forms of test elements. By way of example, essentially square platelets are known, which are also referred to as slides, in whose center a multilayer test area is located. Diagnostic test elements which are in the form of strips are referred to as test strips. The prior art extensively describes test elements, for example in the documents DE-A 197 53 847, EP-A 0 821 233, EP-A 0 821 234 or WO 97/02487, the disclosures of which are hereby incorporated herein by reference in their entireties. The present invention relates to test elements in any desired form, including test elements in the form of strips.

Test element analysis systems which contain a test element holder for positioning of the test element in a measurement position, and a measurement and evaluation device for carrying out a measurement and for determining an analysis result resulting from this are known from the prior art for analytical investigation of a sample on a test element, including WO 00/19185, the disclosure of which is hereby incorporated by reference herein in its entirety.

Further analysis devices are known, for example, from EP 0 618 443 A1 or WO 01/48461 A1, the disclosures of which are hereby incorporated by reference herein in their entireties.

Another exemplary system is the ACCU-CHEK® Compact Plus blood glucose analysis system developed by Roche Diagnostics which measures the blood glucose value using the photometric measurement principle. A color change in a test area on a test element which has previously been wetted with the blood of a patient is in this case detected by an optical measurement module and is electronically converted in the device to a value which is proportional to the blood glucose. The measurement process is started using a switch-on button. A motor in a motor module then rotates the drum, which is used as a supply container, with the test elements around a chamber of the supply container further, and a second motor uses a push rod to push a test element out, so that it can be wetted with blood by the user, outside the device. During the process, the test element remains so far in the analysis device that the test area with the indicator chemistry is positioned over the measurement optics in the measurement module. The measurement optics comprise two diodes, a photocell and a lens. The change in the diffuse reflection is converted by the photocell to a signal current which is processed by an electronic circuit on a printed circuit board, and is displayed as blood glucose value on an LC display. The measurement process is ended by operating the switch-on button again, pushing out the test element and switching the analysis device off. The measurement and drive electronics are supplied with a total voltage of about 3 V from two batteries. In contrast to comparable analysis devices, into which, for example, test elements are supplied from the outside and individual intermediate states have to be operated manually, this device has greater functional integration. Seventeen individual test elements are mounted in the supply container, which is in the form of a drum, and the specification for the test elements is identified automatically by means of a barcode reader in the analysis device. A change in the test element magazine, which is in the form of a drum, is detected via a switch on the housing upper part after opening and closing of the test element magazine holder cover. The required states, such as rotation of the test element magazine through one step and various holding positions during the forward movement of the test element are signaled via sliding contacts and dynamically sprung switching contacts to the electronics on the printed circuit board, without any control function being required by the user. In this context, "dynamically sprung" means force loading and unloading and repeated linear movement during operation. The core of the analysis device for carrying out these electromechanical functions is formed by the motor module. This is used, inter alia, to hold the drive motors and the transmission board. The printed circuit board is screwed to the motor module. For this purpose, all the other contacts between these two assemblies are in the form of detachable static spring contents, for example the contacts for the electrical power supply for the drive motors and for the measurement module. In this context, "statically sprung" means single force loading and linear movement during device assembly. The printed circuit board has four layers, because of the numerous functions which are integrated in the device and must be controlled by the device software.

The analysis devices known in the prior art have a multiplicity of components which make electrical contact. For example, sprung contacts, plug-in contacts, solder contacts or sliding contacts which connect the assemblies printed circuit board, motor module, measurement module, drum cover switch, barcode reader and LCD to one another, are known from the Roche Diagnostics Accu-Chek® Compact Plus. Metallic stamped and bent parts are used for this purpose in the prior art, which must be positioned and mounted on the individual assemblies, thus resulting in a large number of individual components, a large amount of assembly effort, and long tolerance chains. Furthermore, the design freedom of the component which makes electrical contact is restricted when using stamped and bent parts, and often requires larger than desired form factors for the analysis device as a result of the larger and more numerous components.

The object of the present invention is therefore to avoid the disadvantages of the prior art and to provide an analysis device for analysis of a sample on a test element with components which make electrical contact, by ensuring that reliable electrical contact is made with a smaller number of individual parts to be fitted.

SUMMARY

According to the invention, this object is achieved by an analysis device for analysis of a sample on a test element, containing at least one component which makes electrical contact for electrical power or signal transmission and is suitable for making an electrical contact with at least one further component. The component which makes electrical contact is in this case an injection-molded circuit mount (also referred to as a "molded interconnect device" or "MID" or "MID component"). In one embodiment, the component comprises a three-dimensional injection-molded circuit mount.

The analysis device according to the invention can analyze a sample on a test element, for example photometrically and/or electrochemically.

In the analysis device according to the invention, at least one component which makes electrical contact is in the form of a three-dimensional, injection-molded circuit mount which can be produced using one of the methods described herein. The component which makes electrical contact is suitable for producing an electrical contact with at least one further component. In various embodiments, the type of electrical contact can comprise any of a sprung contact, plug contact, sliding contact, solder contact or conductive-adhesive contact. On the basis of an electrical contact such as this, conductor tracks on an injection-molded circuit mount (MID component) lead to an electrical component, for example a sensor, a barcode reader, a further contact, a motor etc. Contacts with both single and multistatic sprung contacts which make contact are referred to as sprung contacts.

According to one embodiment of the present invention, the component which makes electrical contact has at least one sprung contact lug for making contact with the second component, which sprung contact lug comprises a contact lug body composed of injection-molded plastic and a metallic electrical conductor structure. By way of example, PEI (polyetherimide), PA (polyamide), LCP (liquid-crystal polymer), ABS (acrylonitrile butadiene styrene), PC (polycarbonate), PC+ABS (polycarbonate+acrylonitrile butadiene styrene), PBT (polybutyleneterephthalate), PI (polyimide) or PET (polyethyleneterephthalate) may be used as the injection-molded plastic, and, for example, copper, gold or nickel may be used for the metallic electrical conductor structure. The contact lug may make contact with a static, a rotating or a linearly moving further component of the analysis device, in or on the analysis device.

In the analysis device according to the invention, the component which makes contact and is in the form of an injection-molded circuit mount may, for example, be a functional assembly of the analysis device, and the further component, with which electrical contact is made, may be a printed circuit board of the analysis device. Functional assemblies in this case are, for example, a barcode reader arrangement, a housing, a transport unit for test elements, a motor module, a measurement module, a positioning device for a test element magazine, a test element magazine holder which contains a sensor, or a heat-treatment device in a measurement module. The following are several comparative examples of how certain functional assemblies are included in the prior art and how the same functional assemblies are included in embodiments of the present invention. The comparisons are illustrative only and descriptions of embodiments of the present invention including such functional assemblies is not intended to limit the scope of the present invention except as otherwise may be recited in the claims appended to this specification.

A barcode reader arrangement is, for example, contained in the analysis device according to the invention, in order to use the barcode reader to read a barcode on a supply container for test elements which, for example, contains information about the test elements contained therein, and about their optimum evaluation. In the prior art, the barcode reader is normally attached to a printed circuit board arm which projects into a housing section of the analysis device in which a supply container for test elements (test element magazine) may be held. Electrical contact is made with the barcode reader via the lengthened printed circuit board arm, in this case.

In contrast to this, the analysis device according to one embodiment of the invention which is desired to have a barcode reader functional assembly contains a barcode reader arrangement which comprises a housing section of the analysis device in which a barcode reader is arranged, with the housing section containing conductor tracks which run to the barcode reader, and sprung contacts for making contact with a printed circuit board, and with the housing section with the conductor tracks and sprung contacts being an injection-molded circuit mount, in particular a three-dimensional injection-molded circuit mount. In this embodiment, there is no need for the lengthened printed circuit board arm. The barcode reader is connected directly to the housing section (for example by a solder contact) in the housing interior. The housing section itself contains the required conductor tracks and a statically sprung contact for making contact with the printed circuit board, in order to ensure the electrical power supply for the barcode reader. This saves components and assembly steps, resulting in more physical space within the analysis device.

In other embodiment, a positioning device for a test element magazine may be required, such as for automatic removal of a test element from, a test element drum magazine, in order to allow specific access to the test element. A positioning device such as this might, for example, rotate a test element magazine which is in the form of a drum and may be designed as described such as in DE 198 54 316 A1, the disclosure of which is hereby incorporated by reference in its entirety. As soon as the test element magazine is correctly positioned, a test element can be removed from it by a transport unit, and can be transported further in the analysis device.

In the prior art, a positioning device for a test element magazine in the form of a drum is designed, for example, such that a drum wheel which is provided as a drive wheel for the test element magazine rotates with the test element magazine, and the drum rotation is registered by two spring contacts, which are hot-swaged to a transmission board, and a segmented sliding ring on the drum wheel (a total of five individual components to be fitted).

According to one embodiment of the present invention, an analysis device according to the invention might contain a positioning device for a test element magazine, which positioning device comprises a board for supplying electrical power (including electrical signals) and a drive wheel, which is driven by a motor, for driving the rotatable test element magazine, with the board being designed with spring contacts as an injection-molded circuit mount, and with the drive wheel being formed with a segmented disk, with which electrical contact can be made, as an injection-molded circuit mount. The five individual components are therefore replaced by two MID components. In this case, furthermore, this offers the advantage of more flexible configuration of the physical space in the analysis device according to the invention, by freer shaping of a plastic part and of the conductor tracks arranged on it, using MID technology.

A transport unit for test elements is used in an analysis device for analysis of a sample on a test element for transport of a test element in the analysis device, for example from a test element magazine to a sample feed position and to a measurement position. One such transport unit is known, for example, from DE 199 02 601 A1 relating to removing an analytical consumable, in particular a test element, from a supply container with chambers which are closed by films and from which the consumable is pushed out by a plunger, the disclosure of which is hereby incorporated herein by reference in its entirety.

The plunger (push rod) is moved in the axial direction by a motor. In this disclosure, the push rod has a guide bush at one end, which is guided in a guide device during movement of the push rod. The guide device has a contact component which is in the form of a stamped and bent part and has three contact lugs which are used to position the guide bush and therefore the push rod. Depending on the position of the guide bush, the contact lugs are pressed by the guide bush against contact surfaces on a printed circuit board.

According to one embodiment of the present invention, the analysis device according to the invention contains a transport unit for test elements, which transport unit comprises a push rod for transport of a test element within the analysis device, with the push rod having a guide bush which can be guided in a guide device during transport of the test element. In this case, the guide bush has sprung contact lugs for making contact with a printed circuit board, and the guide device has switching elements which are arranged such that they press the contact lugs against the printed circuit board in specific positions of the guide bush in the guide device, with the guide bush with the contact lugs being an injection-molded circuit mount (in particular a three-dimensional injection-molded circuit mount). The switching function is therefore integrated in the guide bush, whose contact lugs are, for example, pressed by injection-molded switching studs on the guide device against the printed circuit board contacts. This not only saves manufacturing, positioning and assembly steps in comparison to the prior art, but it is also possible to save space in the corresponding configuration of the guide bush.

Largely automated analysis devices for analysis of a sample on a test element in the prior art contain motor modules which have motors. These motors are electric motors and are used, for example, for positioning a test element magazine or for driving a push rod which moves a test element within the analysis device.

In the prior art, a contact plate is pressed into a motor holder in order to supply electrical power to a motor (drum motor or push-rod motor), with the contact plate having produced an electrically conductive connection to a printed circuit board via sprung contact lugs.

According to one embodiment of the present invention, the analysis device according to the invention contains a motor module which comprises a motor and a motor holder, with the motor holder having contact lugs for making contact with a printed circuit board, and with the motor holder with the contact lugs being an injection-molded circuit mount, in particular a three-dimensional injection-molded circuit mount. The contact lugs of the MID part may be soldered to a printed circuit board. Manufacturing and assembly steps can be saved by using the injection-molded circuit mount. In particular, the motor holder can be made simpler since, for example, there is no need for injection-molded domes for holding the separate contact plate.

An analysis device for analysis of a sample on a test element, which can hold a test element magazine in a test element magazine holder in order to supply a multiplicity of test elements, may also, according to the invention, contain a sensor in the test element magazine holder which detects any change in the test element magazine. In the case of analysis devices from the prior art, a change in the magazine is registered as soon as the analysis device cover, which covers the test element holder, is opened and then closed, since a locking switch on the printed circuit board is operated during this process. However, if the analysis device cover is opened and closed without the magazine being changed, the device registers a magazine change even though this has not taken place. In consequence, the magazine is rotated for identification by the barcode reader and in order to find a chamber which is filled with the test element without this being necessary. A sensor for detecting an actual magazine change is not provided in the prior art since the point at which the magazine change would be detected cannot be accessed via the two-dimensional printed circuit board provided in the analysis device, and it is not financially feasible to make contact, for example via soldered-on, flexible cables.

According to one embodiment of the present invention, the analysis device according to the invention comprises a test element magazine holder which contains a sensor and contains electrical conductor tracks which run to the sensor, with the test element magazine holder with the conductor tracks being an injection-molded circuit mount, in particular a three-dimensional injection-molded circuit mount. A signal can then be passed via electrical conductor tracks to the printed circuit board if the sensor has been activated, for example by closing a contact on removal of the magazine.

An analysis device for analysis of a sample on a test element may contain a heat-treatment device in order to heat treat a test element before and during analysis (for example for a measurement of blood clotting). Both heaters on the device side (for example in a measurement module in which a measurement is carried out with the sample on the test element) and heating elements integrated in the test element (for example from DE 103 59 160 A1 the disclosure of which is hereby incorporated by reference herein in its entirety) are known in the prior art. Heaters on the device side may be ceramic elements which are mounted in the test element holder or are incorporated in the test element holder during its production process. Fitted heating elements frequently lead to leakage problems, however. It is possible for a liquid to enter the device, and lead to damage. Further problems occur when contamination occurs from sample material. Furthermore, a plurality of assembly steps are necessary in order to obtain the finished assembly. The use of ceramic heaters generally has the disadvantage that ceramic can fracture, so that the serviceability of the device is not ensured. Furthermore, the use of integrated ceramic heaters places stringent demands on the manufacturing methods that are used, and considerably increases their complexity.

According to one embodiment of the present invention, the analysis device according to the invention contains a test element holder for holding a test element (for example during a measurement), which contains a heat-treatment device for heat-treatment of the test element, with the heat-treatment device comprising heating filaments and being an injection-molded circuit mount, in particular a three-dimensional injection-molded circuit mount. The conductor tracks which are used as heating filaments are therefore integrated directly by means of MID technology in the plastic of the test element holder. There is no need for integration of a ceramic heater. The contacts for supplying electrical power to the heating filaments may be produced, for example, from metallic stamped or bent parts or likewise by means of the MID method. They allow a heat-treatment device to be connected to a printed circuit board for supplying electrical power. The advantages of this embodiment of the analysis device according to the invention with a heat-treatment device are simplicity of the production process, avoidance of problems resulting from ceramic fracture, reduction in the production costs by the lack of ceramic manufacture, a sealed test element holder, and that complex and miniaturized forms are possible.

According to a further embodiment of the present invention, the analysis device according to the invention contains a measurement module for carrying out a measurement on an analyte which is contained on a test element, which measurement module comprises a test element holder for holding the test element during the measurement which test element holder contains a heat-treatment device for heat-treatment of the test element, with the test element holder with the heat-treatment device, which comprises heating filaments and a spring contact, being an injection-molded circuit mount, in particular a three-dimensional, injection-molded circuit mount. The conductor tracks, which are used as heating filaments, are therefore integrated directly in the plastic of the test element holder by means of MID technology. The integration of a ceramic heater is not essential. The sprung contacts, which are likewise produced by the MID method, allow the heat-treatment device to be connected to a printed circuit board for supplying electrical power. There is therefore no need to use pins. As a result, the entire production process for the heat-treatment device is advantageously restricted to plastic molding by injection-molding and to the application of the metallic structure to the MID component. The advantages of this embodiment of the analysis device according to the invention with a heat-treatment device are simplification of the production process, avoidance of the problems resulting from ceramic fracture, reduction in the production costs owing to the lack of ceramic manufacture, a sealed test element holder and that complex and miniaturized forms are possible.

An analysis device for analysis of a sample on a test element contains at least one test element holder in order to position a test element before and during analysis (for example for holding the sample and in particular for electrochemical or optical analysis of the sample). According to one embodiment of the present invention, the test element holder has at least two sprung contacts which are used for positioning a test element in the test element holder, with the test element holder with the at least two sprung contacts being an injection-molded circuit mount (in particular a three-dimensional, injection-molded circuit mount). The positioning process can be carried out with the aid of a test element holder such as this, for example in such a way that a metallic electrically conductive structure (for example a metallic area) which is provided on the test element shorts the at least two sprung contacts as soon as the test element is located in the desired position. An electric current can flow through the short via the contacts, and can be detected and evaluated as a position signal.

According to one embodiment of the present invention, the analysis device according to the invention contains a contact element for test element evaluation in the analysis device, in the form of a component which makes electrical contact and is an injection-molded circuit mount (such as a three-dimensional injection-molded circuit mount). This contact element for test element evaluation can make contact with a test element to be evaluated electrochemically.

Electrochemical methods for determining the concentration of an analyte are based, for example on current or charge measurement. Methods such as these are known, for example, from the documents U.S. Pat. No. 4,654,197, EP 0 505 475 B or U.S. Pat. No. 5,108,564, the disclosures of which are hereby incorporated by reference in their entireties. Electrical signals must be transmitted between the test element and the analysis system in order to carry out electrochemical analysis. Electrical contact must therefore be made with a test element that has been introduced into an analysis system, in the analysis system with the aid of an electrical connection system.

The prior art makes use of a plug connector as a contact element for making contact, comprising a plastic part and metallic elements. The plastic part is used as a housing and provides the guide function for the test element. The metallic elements are used for carrying electrical power and to make contact. The metallic elements are produced by bending and stamping processes and are either fitted to the plastic part or are molded directly in it. The limitations for the design and configuration of a plug connector result mainly from the restrictions of the stamping and bending processes and the requirement to allow metal parts to be fitted and extrusion-coated. As a result of the stamping and bending processes, the configuration and design of the contact elements in the prior art is greatly restricted in comparison to the capabilities of plastic processes. In addition, the requirement to allow metal parts to be fitted and to be extrusion-coated must be taken into account in the design. In the analysis device according to the invention, the function of making electrical contact is not provided by fitted metal parts, but is provided by a contact element produced using MID technology.

According to one embodiment of the invention, the analysis device according to the invention contains a contact element for test element evaluation, which contact element has a contact surface for a test element, with a multiplicity of contact ramps projecting over the contact surface and being intended to make electrical contacts with a test element which is positioned on the contact surface, and which can be connected to a printed circuit board via conductor tracks which run on the contact element, with the contact element being an injection-molded circuit mount, in particular a three-dimensional injection-molded circuit mount. A test element which is to be analyzed electrochemically can be moved in a slotted guide of the analysis device on the contact surface of the contact element until it is positioned on the contact ramps such that they press against the test element and make contact with the electrical contacts of the test element. By way of example, the contact ramps may be in the form of projections, which are arranged on an extension of the contact surface and are in the form of ramps, or in the form of individual sprung contact lugs in the form of ramps. The conductor tracks runs on the contact element, for example to one end of the contact element, where they are soldered to the printed circuit board in order to supply electrical power and for signal processing.

According to one embodiment of the present invention, the contact element for test element evaluation is integrated in the housing of the analysis device, with the housing including the contact element being an injection-molded circuit mount, such as a three-dimensional injection-molded circuit mount.

According to another embodiment of the present invention, the contact element for test element evaluation is integrated in a test element magazine. In this case, an individual contact or a way of making contact for all the test elements contained in the magazine may be provided for each test element. An interface to the analysis device is also located on the magazine. The test elements are finally connected to the device via this interface. This embodiment has the advantages that it allows a space-saving design since there is no need for accurate positioning of the individual test elements with respect to the analysis device, and the way in which contact is made in the magazine can be designed to save costs, since all that is necessary is a single way of making contact with the restricted number of test elements contained in the magazine, and the contact element is then disposed of with the magazine.

The present invention also relates to a supply container for at least two test elements (test element magazine) with the test elements having electrical conductor tracks and the supply container containing electrical contacts for making contact with the conductor tracks of a test element contained therein, during the electrochemical analysis of a sample on the test element.

By way of example, the supply container is a test element magazine which is in the form of a drum and, in particular, can be designed largely in the same way as the supply container described in DE 198 54 3.16 A1, the disclosure of which is hereby incorporated herein by reference in its entirety. The supply container according to the invention has electrical contacts which are used to make electrical contact with a test element to be evaluated electrochemically. The supply container according to one embodiment of the present invention has at least two separate chambers for holding the test elements, with electrical contacts for making contact with the conductor tracks of the respective test element contained therein being arranged in each chamber during the electrochemical analysis of a sample on the test element.

In the prior art, the electrochemical evaluation is carried out in a measurement module of the analysis device, in which electrical contact is made with the test element and which is arranged at a distance from the test element supply container in the analysis device. If required, the test elements are fed automatically through a transport unit in the analysis device from the test element supply container, are transferred to the measurement module and are positioned accurately there, in order to make electrical contact. One disadvantage of making electrical contact in this way in a measurement module is, for example, that it requires a larger physical space within the analysis device for electrochemical analysis of the test element. Furthermore, the test element must be positioned accurately, in order to make contact. The transfer of the test element to the contact-making point in the analysis device is a potential weakness in terms of positioning, reliability and dynamic contact-making. The contacts of the measurement module in the analysis device are also suitable only for one specific electrode structure on test elements.

In contrast, the solution according to the embodiments of the present invention has the advantage, which results from the integration of the electrical contact-making process in the supply container (test element magazine), that this allows a simple interface, which can be standardized, between the analysis device and the magazine, in which case the electrical contacts which, for example, are arranged in the chambers of the respective magazine can be matched to the electrode structure of the test elements contained therein, and can be designed to be variable. This also allows the analysis device and magazine to be designed to save space. Furthermore, there is no need for accurate positioning of the test element outside the supply container in the analysis device. The process of making contact with the test elements in the magazine can be designed to save costs, since it need make contact only with the test elements contained in the magazine, and the magazine can then be disposed of.

Contact can be made in the supply container via fitted or extrusion-coated metal parts. According to one embodiment of the present invention, the supply container according to the invention with the electrical contacts is essentially an injection-molded circuit mount, such as a three-dimensional injection-molded circuit mount.

The necessary electrode structure for test elements to be evaluated electrochemically is generally produced in the prior art by a printing method or by laser ablation. This is done by first of all producing the test element, and then applying the electrode structure. This means that a three-dimensional configuration of the test element is greatly restricted, or impossible. Relatively large test elements can therefore be produced only with difficulty, with multiple tests or tests for different parameters, since laser ablation restricts the size of the illumination window, and printing methods very greatly limit the design options.

The invention therefore also relates to a test element containing a test area for electrochemical analysis of a liquid sample in an analysis device, with the test area on the test element being connected to electrical conductor tracks, and with the test element with the electrical conductor tracks being essentially an injection-molded circuit mount.

In the solution according to the invention, the electrode structure is integrated in a plastic sample mount by means of an MID method. This results in the advantages of a high level of design freedom for the configuration of the test element (real 3D structures are possible), a simple production process (injection-molding) and that it is possible to produce large test elements with a large number of test areas.

The invention also relates to a method for producing an analysis device for analysis of a sample on a test element, containing at least one component which makes electrical contact electrical power transmission, which is suitable for making an electrical contact with at least one further component for having the following steps: producing the component which makes electrical contact and comprises a base body and a metallic conductor structure, by means of a method for producing injection-molded circuit mounts, and positioning and mounting the component which makes electrical contact in the analysis device in order to make an electrical contact with the further component with which contact is made.

The method for producing injection-molded circuit mounts, typically comprises one of the following methods: two-component injection-molding, hot stamping, in-mold film coating and laser structuring.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which:

FIG. 1.1 illustrates a perspective view of an analysis device from the prior art.

FIG. 1.2 illustrates an exploded view of the analysis device from FIG. 1.1.

FIG. 3.1 illustrates an exploded view of a prior art positioning device for a test element magazine in an analysis device.

FIG. 3.2 illustrates an exploded view of an embodiment of a positioning device for a test element magazine in an analysis device according to the present invention.

FIG. 4.1 illustrates an exploded view of a prior art transport unit for test elements in an analysis device.

FIG. 4.2 illustrates an exploded view of an embodiment of a transport unit for test elements in an analysis device according to the present invention.

FIG. 5.1 illustrates an exploded view of a prior art motor module in an analysis device.

FIG. 5.2 illustrates a perspective view of an embodiment of a motor holder of a motor module in an analysis device according to the present invention.

FIG. 6.1 illustrates a perspective view of a prior art barcode reader arrangement in an analysis device.

FIG. 6.2 illustrates a perspective view of an embodiment of a barcode reader arrangement in an analysis device according to the present invention.

FIG. 7.1 illustrates an exploded view of a prior art test element magazine holder in an analysis device.

FIG. 7.2 illustrates a perspective view of an embodiment of a test element magazine holder with a sensor in an analysis device according to the present invention.

FIG. 11.1 illustrates a perspective view of a prior art a heat-treatment device in a measurement module of an analysis device.

FIG. 11.2 illustrates a perspective view of the rear face of a heating element from the prior art.

FIG. 11.3 illustrates a perspective view of the front face of a heating element from the prior art.

FIG. 11.4 illustrates a perspective view of an embodiment of a heat-treatment device in a measurement module of an analysis device according to the present invention.

Figure 2:
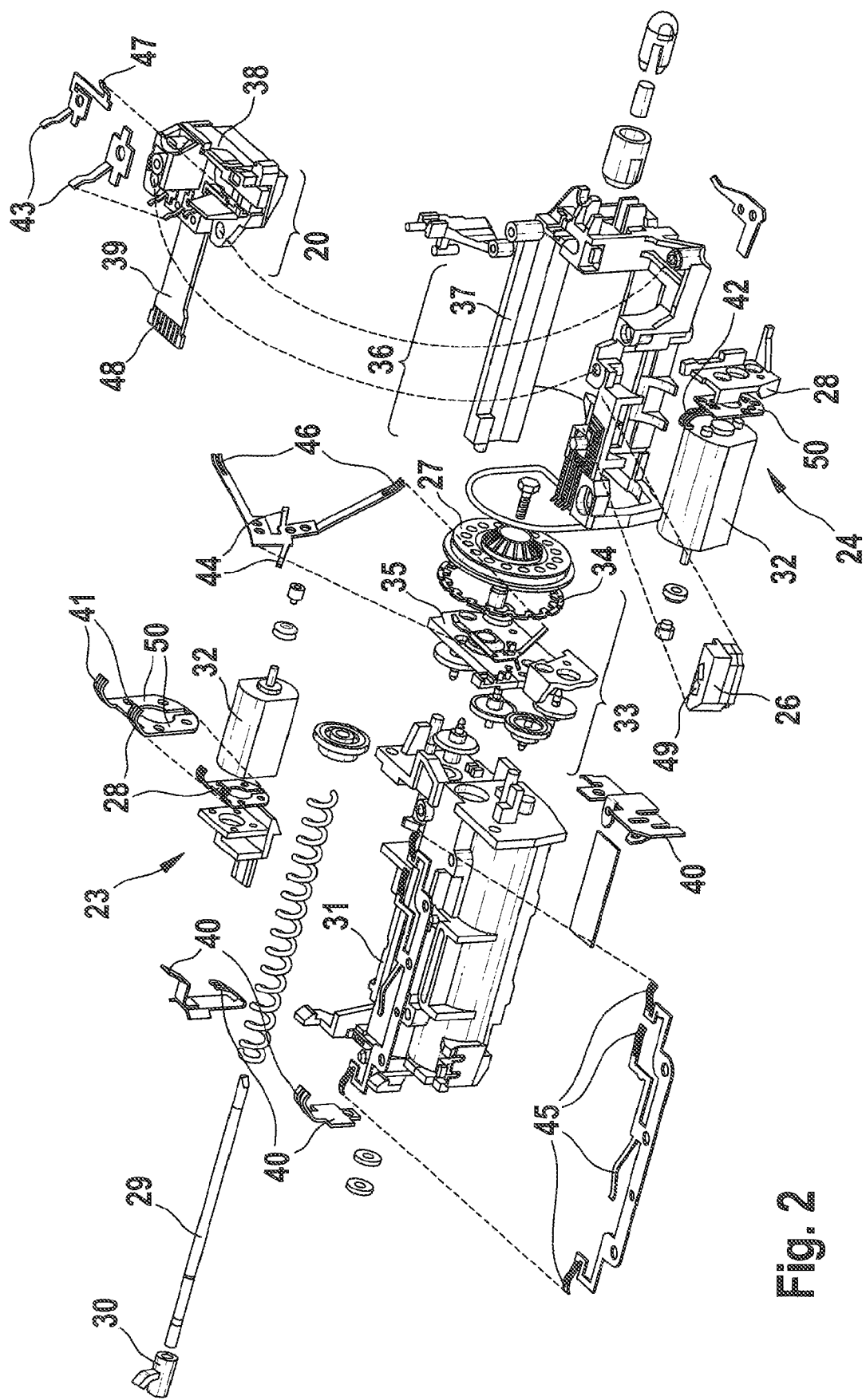
FIG. 2 illustrates an exploded view of various functional assemblies of an analysis device from the prior art.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

The analysis device 1 has a housing 2 which contains a display area 3 (LCD 4) and a control area 5 (switch-on button 6). The test element magazine holder 7 can be seen in the analysis device 1 illustrated in FIG. 1.1, because a test element magazine holder cover has been removed. A test element magazine 8 which is in the form of a drum and can hold a plurality of test elements is located in the test element magazine holder 7. On the outside, the test element magazine has a barcode 9 which contains information, for example about the test elements contained in it, and which can be read by a barcode reader (which is not illustrated). A measurement process is started using the switch-on button 6. A motor (which cannot be seen) rotates the test element magazine 8 further around a chamber 10, and a second motor (which cannot be seen) uses a push rod to move a test element 11 out of a chamber 10 of the test element magazine 8 until it projects out of the analysis device 1. In this position, a user can pass a sample (for example blood) to the test element 11. Measurement optics (which cannot be seen) in the analysis device 1 analyze the sample on the test element 11. The analysis result (for example a blood glucose value) is displayed on the LC display. A removable piercing aid 12 is fitted at the side to the housing 2 of the analysis device 1, and can be used to obtain samples.

FIG. 1.2 shows an exploded illustration of the analysis device from FIG. 1.1.

From top to bottom, the illustration shows the test element magazine holder cover 7, the upper housing half 14, the LC display 4, the printed circuit board 15, the measurement module 20, the motor module 16, the lower housing half 17, the name plate 18, the battery compartment cover 19 and the piercing aid 12. The lower housing half 17 has a cover 21 which can be folded up and can be opened and unlocked with the aid of the unlocking knob 22. A test element magazine can then be inserted into, or removed from, the test element magazine holder 7. The motor module 16 has a push-rod motor module 23 and a magazine motor module 24. The magazine motor module 24 has, inter alia, the drive wheel 27 which extends into the test element magazine holder 7 and has a tooth system for engaging in a test element magazine to be driven. The printed circuit board 15 has a printed circuit board arm 25, which extends into the test element magazine holder 7 and to which, inter alia, a barcode reader 26 is attached.

FIG. 2 shows an exploded illustration of various assemblies of an analysis device from the prior art.

The various assemblies have a plurality of electrical contacts for electrical power transmission. For purposes of this disclosure, "electrical power transmission" is intended to include transmission not only of electrical power but also electrical signals; that is, an electrical transmission between components for any useful purpose, including providing or transferring power for operation of a component or transmitting electrical signals used by a component, such as electrochemical measurement signals.

For classification purposes, a distinction is drawn between sprung contacts, plug contacts, solder contacts and sliding contacts. To distinguish between them electronically, these contacts are subdivided on the basis of the current load into signal transmission and power current transmission. Furthermore, the sprung contacts are mechanically subdivided into statically springing and dynamically springing contacts. FIG. 2 shows the various contact types which connect the assemblies motor module 16, measurement module 20 and barcode reader 26 to one another and to the printed circuit board (which is not illustrated). In detail, FIG. 2 illustrates the following components:

a) A transport unit for test elements has a push rod 29, a guide bush 30 and a guide device 31, in which the guide bush 30 can be guided. The method of operation of the transport unit will be explained in more detail with reference to FIG. 4.1.

b) A push-rod motor module 23 has a motor holder 28 and a motor 32.

c) A magazine motor module 24 likewise has a motor holder 28 and a motor 32. The motor modules will be explained in more detail with reference to FIG. 5.1.

d) A positioning device 33 for a test element magazine has a drive wheel 27, a segmented disk 34 and a transmission board 35. The positioning device will be explained in more detail with reference to FIGS. 3.1 and 3.2.

e) A barcode reader arrangement 36 has a housing section 37 and a barcode reader 26, which is attached to a printed circuit board arm (which is not illustrated) which projects into the housing section 37. The barcode reader arrangement 36 will be explained in more detail with reference to FIG. 6.1.

f) A measurement module 20 has a test element holder 38 and an optics board 39.

Inter alia, the assemblies have the following electrical contacts: battery contacts 40, magazine motor contact 41, push-rod motor contact 42, measurement module contact 43, position switch contacts 44 for the drive wheel 27, push-rod switch contacts 45, sliding contacts 46 for the drive wheel 27, test element contact 47 in the measurement module 20, optics board contact 48 in the measurement module 20, barcode reader contact 49, motor contacts 50 and a magazine position contact in the form of the segmented disk 34.

This analysis device from the prior art has more than 67 contacts, which are provided by more than 19 separate components. In the analysis device according to the invention, these separate components and the assembly steps associated with them can largely be saved by integrating them in MID components which make electrical contact.

FIG. 3.1 shows an exploded illustration of a positioning device for a test element magazine in an analysis device from the prior art.

The positioning device 33 has a transmission board 35, a metallic segmented disk 34 and a drive wheel 27. The drive wheel 27 is rotated with the aid of a motor (which is not illustrated). A test element magazine (which is not illustrated) is also rotated by the tooth system 52 on the drive wheel 27. In the prior art, the rotation of the test element magazine is detected by the two sliding contacts 46, which are hot-swaged on the transmission board 35, on the segmented disk 34. The signal is passed to a printed circuit board (which is not illustrated) by means of two further position switch contacts 44.

FIG. 3.2 shows a positioning device 33 for a test element magazine in an analysis device according to the invention. Instead of having five separate components, this positioning device has just two components: the board 53 (component 123 which makes electrical contact) which is an injection-molded circuit mount, and the drive wheel 54 (component 124 which makes electrical contact), which is likewise an injection-molded circuit mount. Spring contacts 55 are integrated in the MID board 53, 123 and are used to make contact with the segmented disk 56 and a further printed circuit board (which is not illustrated). The segmented disk 56 is integrated in the drive wheel 54, 124.

FIG. 4.1 shows a transport unit for test elements in an analysis device from the prior art.

The transport unit 57 has a push rod 29 by means of which a test element can be moved in the axial direction 58. The push rod 29 is driven by a push-rod motor (which is not illustrated). The push rod 29 has a guide bush 30 which is guided in a longitudinal hole 59, which is open at the top, in the guide device 31. A spacer 60 is fitted to the guide bush 30 and projects upwards. A push-rod switch contact 45 which is in the form of a metallic stamped and bent part is mounted on the guide device 31. The three contact lugs 61 of the push-rod switch contact 45 are pressed in three different positions of the guide bush 30 in the longitudinal hole 59 through the spacer 60 upwards against the contact surfaces of a printed circuit board (which is not illustrated), such that the respective position is identified.

FIG. 4.2 shows a transport unit for test elements in an analysis device according to the invention.

This transport unit also has a guide bush 62 for the push rod 29 (which is not illustrated), and a guide device 63 matched to it. The guide device 63 contains a longitudinal hole 64, which is open at the top, and in which the guide bush 62 is guided. The guide bush 62 has contact lugs 65 which are sprung in the direction 66. The guide bush 62 (component 125 which makes electrical contact) with the contact lugs 65 connected via a spacer 67 is an injection-molded circuit mount (MID). The guide device 63 is an injection-molded part and has switching elements 68 which press the contact lugs 65 upwards against contact surfaces on a printed circuit board (which is not illustrated) in three different positions of the guide bush 62. These three positions can therefore be identified by the analysis device.

FIG. 5.1 shows an exploded illustration of a motor module in an analysis device from the prior art.

By way of example, the motor module 69 may be a push-rod motor module or a magazine motor module and has a motor 32 and a motor holder 28. A contact plate 70 is pushed into the motor holder 28 in order to supply electrical power to the motor 32, and makes an electrically conductive connection to a printed circuit board (which is not illustrated) via sprung contact lugs 71.

FIG. 5.2 shows a motor holder of a motor module in an analysis device according to the invention.

The motor holder 72 (component 126 which makes electrical contact) is an injection-molded circuit mount (MID). The motor holder 72 and the electrical contacts, in the form of contact lugs 73 with the conductor tracks 74 originating from them, are integrated in this MID component which makes electrical contact. The contact lugs 73 can be soldered to a printed circuit board.

FIG. 6.1 shows a barcode reader arrangement in an analysis device from the prior art.

A barcode reader 26 is attached to a printed circuit board arm 25 on the printed circuit board 15, is supplied with electrical power via the printed circuit board 15, and emits signals via it. The printed circuit board arm 25 also has further components 75, which will not be explained in any more detail. The barcode reader 26 is arranged on the printed circuit board arm 25 such that it projects into a test element magazine holder (which is not illustrated) in order to be able to read the barcode there, on the respectively accommodated test element magazine.

FIG. 6.2 shows a barcode reader arrangement in an analysis device according to the invention.

The barcode reader arrangement 76 comprises a housing section 76 of the analysis device according to the invention, in which a barcode reader 26 is arranged. The housing section 77 contains conductor tracks 78, which run to the barcode reader 26, and sprung contacts 79 for making contact with a printed circuit board (which is not illustrated). The housing section 77 (component 127 which makes electrical contact) with the conductor tracks 78 and the sprung contacts 79 is a three-dimensional, injection-molded circuit mount. Since, in this embodiment, electrical power is passed to and from the barcode reader 26 by the MID housing section 77, there is no need for the printed circuit board arm 25 from the prior art (see FIG. 6.1) (provided that a different solution is likewise found for further components 75 in FIG. 6.1). This saves physical space in the analysis device, and the printed circuit board can be produced in more advantageous batches and with little scrap.

FIG. 7.1 shows a test element magazine holder in an analysis device from the prior art.

A test element magazine 8 can be inserted into the test element magazine holder 7. In the analysis device from the prior art, a change of test element magazine 8 is registered by opening and closing a test element magazine holder cover (which is not illustrated), thus operating a locking switch 80. If the test element magazine holder cover is opened and closed without the test element magazine 8 being changed, then the analysis device incorrectly registers that the test element magazine 8 has been changed.

FIG. 7.2 shows a test element magazine holder with a sensor for identification of a test element magazine change in an analysis device according to the invention.

In the analysis device according to the invention, a change of test element magazine 8 is identified when a mandrel sleeve 81 which supports the test element magazine 8 at the point 82 has been unlocked by a bolt 83, has been moved in the opening direction 84 and, after the test element magazine cover has been closed, has been moved back again in the closing direction 85. A sensor 86 for identifying this movement sequence is designed, for example, such that a switching stud (which is not illustrated) on the mandrel sleeve 81 makes a contact, and passes on the signal via spring contacts 87 to the printed circuit board (which is not illustrated). This largely avoids incorrect identification of a change of the test element magazine 8. The test element magazine holder 89 (component 128 which makes electrical contact) in this embodiment contains the spring contacts 87 and conductor tracks 88, which connect the spring contacts 87 to the sensor 86, and is a three-dimensional injection-molded circuit mount (MID).

Figure 8:
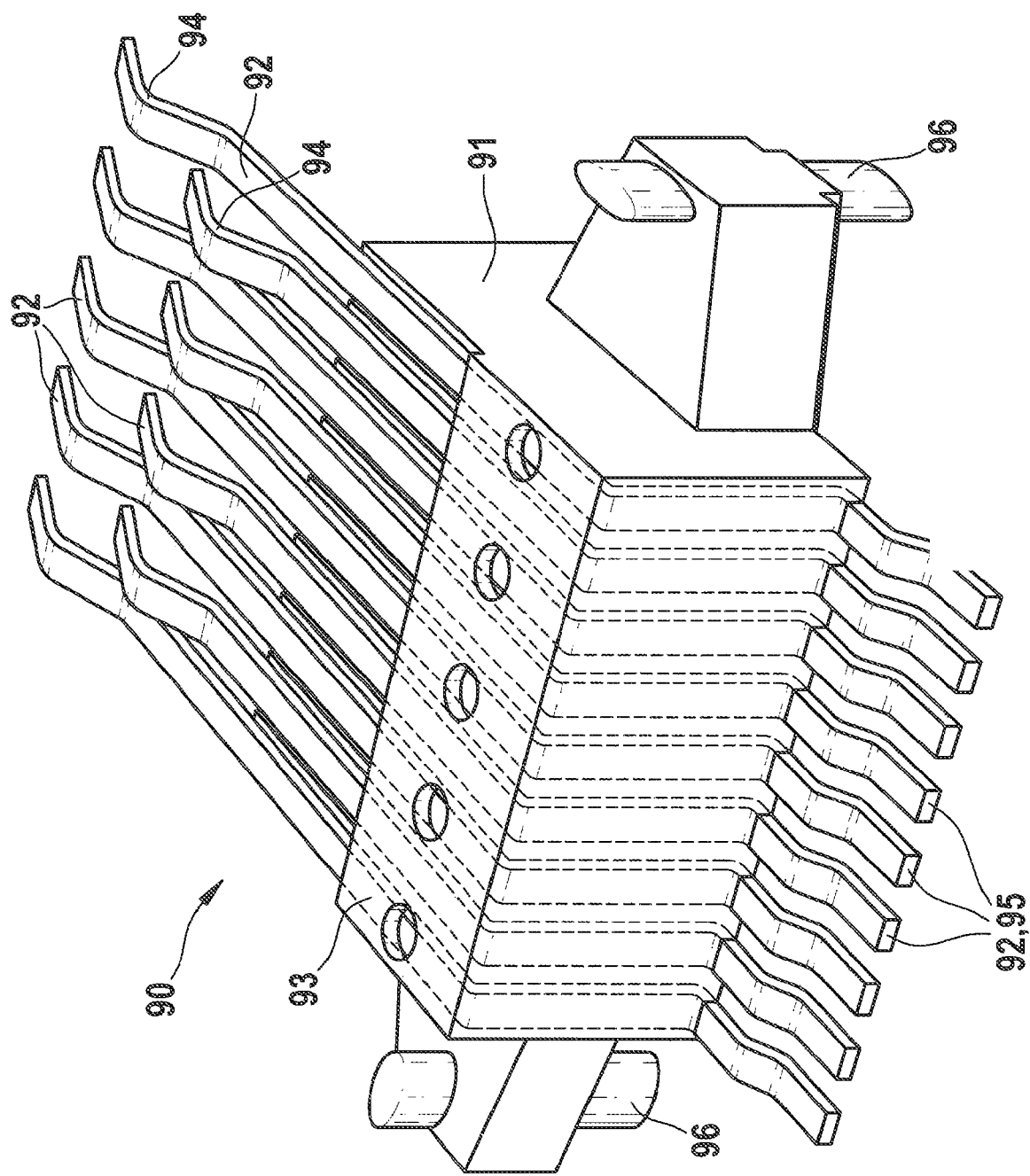
FIG. 8 illustrates a perspective view of a prior art contact element for test element evaluation in an analysis device.

FIG. 8 shows a contact element for test element evaluation in an analysis device from the prior art.

The contact element 90 is used to make electrical contact with a test element which is to be evaluated electrochemically (but which is not illustrated). The contact element 90 is formed from a plastic part 91 and metallic elements 92. The metallic elements 92 are produced by bending and stamping processes, and are fitted to or directly injection-molded on the plastic part 91. In order to make contact, a test element is moved in the direction of the contact ramps 94 on the contact surface 93 until the contact ramps 94 press against contact surfaces which are provided on the test element, and thus make contact with them. The contact lugs 95 are firmly soldered to the printed circuit board in the analysis device. The plugs 96 are used to align the contact element 90 while it is being fitted in the analysis device. The design and configuration of this contact element from the prior art are subject to limitations resulting from restrictions in the stamping and bending processes and the requirements to be able to fit and extrusion-coat the metallic elements.

Figure 9:
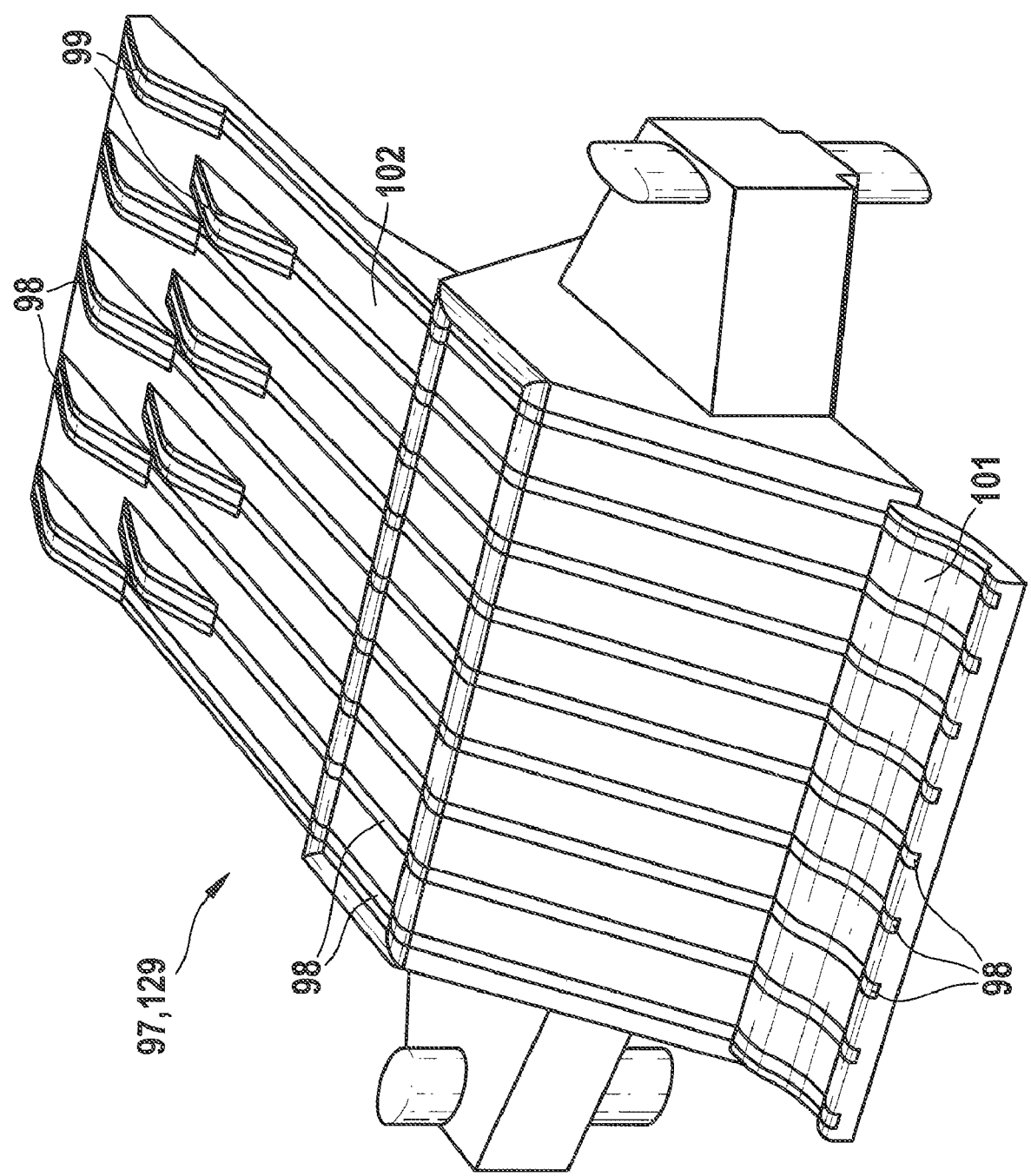
FIG. 9 illustrates a perspective view of an embodiment of a first contact element for test element evaluation in an analysis device according to the present invention.

FIG. 9 shows a first contact element for test element evaluation in an analysis device according to the invention.

This contact element 97 (component 129 which makes electrical contact) is a three-dimensional injection-molded circuit mount (MID). The conductor tracks 98 and contact ramps 99 are in the form of electrically conductive areas directly on the injection-molded plastic part 100. The conductor tracks 98 run from a contact lug 101, which can be connected to a printed circuit board, over a test element contact surface 102 to the contact ramps 99. The contact ramps 99 are formed by plastic projections on a surface of the plastic part 100, with the metallic conductor tracks 98 running on the plastic projections.

Figure 10:
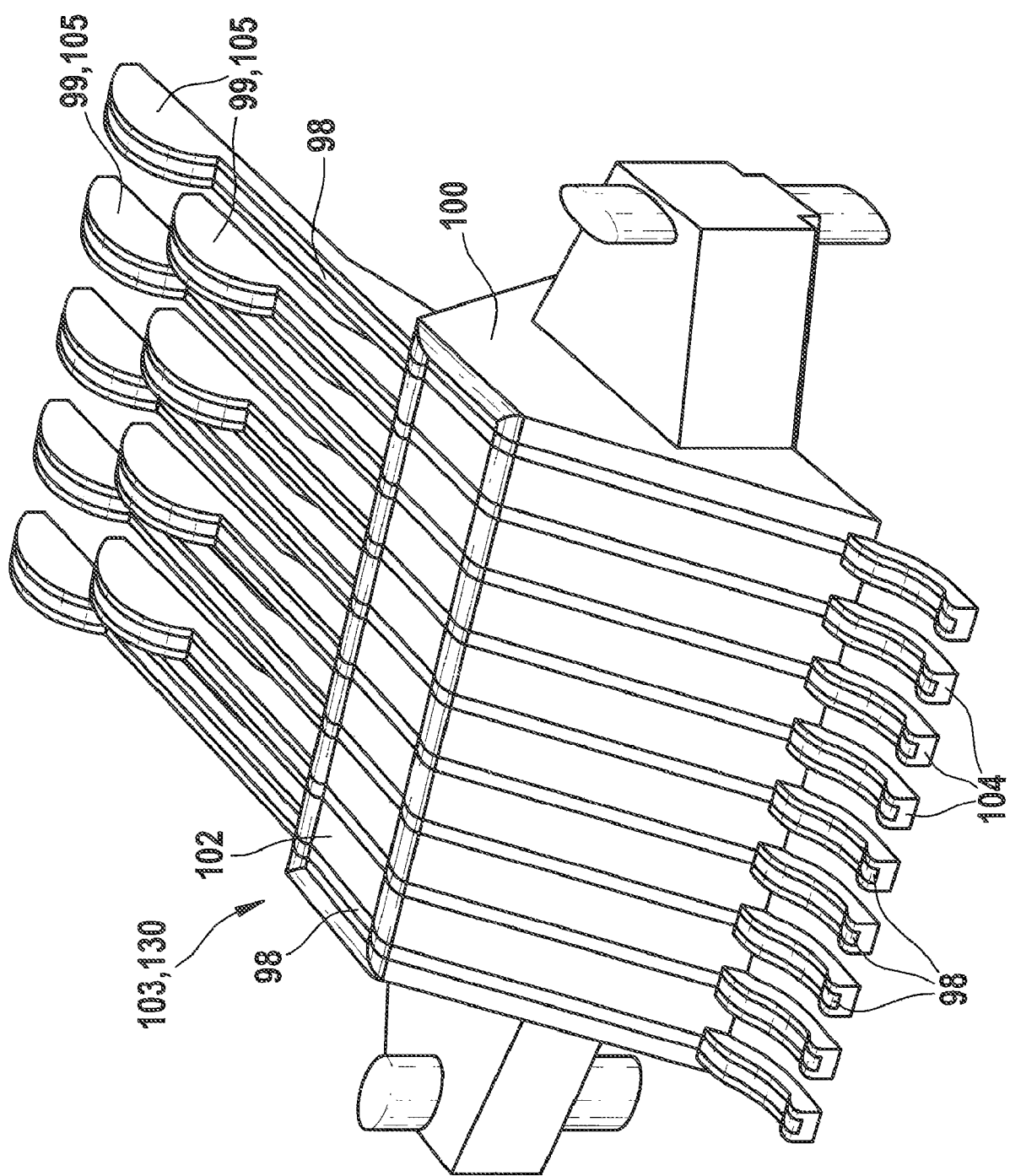
FIG. 10 illustrates a perspective view of another embodiment of a contact element for test element evaluation in an analysis device according to the present invention.

FIG. 10 shows a second contact element for test element evaluation in an analysis device according to the invention.

This contact element 103 (component 130 which makes electrical contact) is likewise a three-dimensional injection-molded circuit mount (MID) with conductor tracks 98 and contact ramps 99 on an injection-molded plastic part 100, which has a test element contact surface 102. In contrast to the embodiment shown in FIG. 9, separate contact lugs 104 and separate contact ramps 105 are in this case provided for each of the conductor tracks 98.

FIG. 11.1 shows a heat-treatment device in a measurement module of an analysis device from the prior art.

A ceramic heating element is mounted, or is incorporated directly during the production process, in an analysis device housing half 106. The electrical connections 107 of the ceramic heating element can be seen in FIG. 11.1.

The ceramic healing element 108 is shown from the rear face in FIG. 11.2 and from the front face in FIG. 11.3. For the sake of simplicity, FIG. 11.3 shows only two of the four electrical connections 107. The two connections 107 are connected to a heating filament 109 on a ceramic plate 110.

FIG. 11.4 shows a heat-treatment device in a measurement module of an analysis device according to the invention.

The measurement module 111 is arranged in the analysis device housing half 112 and has a test element holder 113 in which a heat-treatment device 114 is integrated. The test element holder 113 (component 131 which makes electrical contact) contains heating filaments 115 and a sprung contact 116, and is a three-dimensional injection-molded circuit mount.

Figure 12:
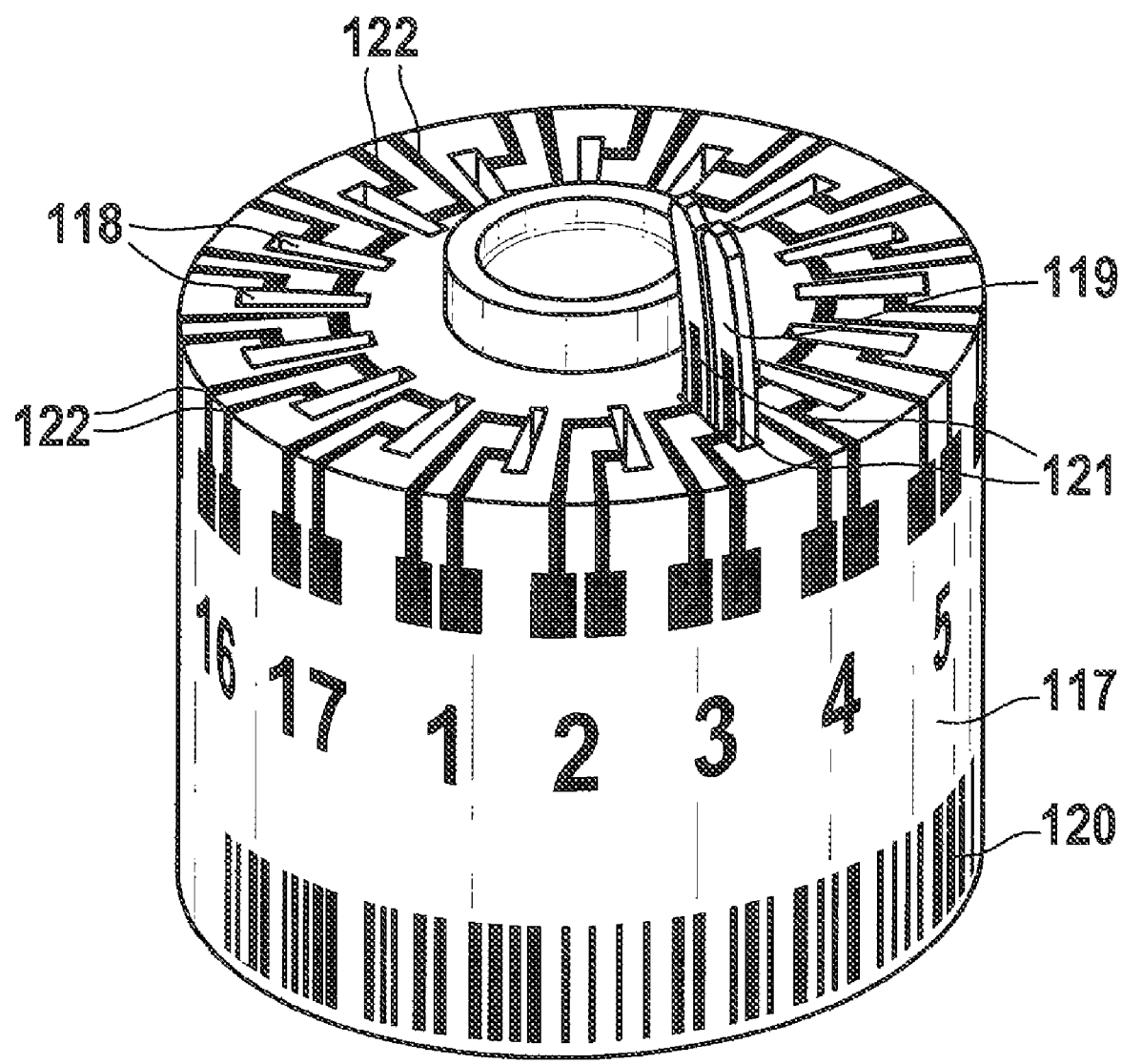
FIG. 12 illustrates a perspective view of an embodiment of a supply container according to the present invention for test elements in an analysis device.

FIG. 12 shows a supply container according to the invention for test elements in an analysis device.

The supply container 117 is a test element magazine which is in the form of a drum and has 17 separate chambers 118 for holding 17 test elements 119 in the form of strips. The supply container 117 has a barcode 120 on its outer face. The test elements 119 are test elements 119 which can be evaluated electrochemically and are provided with electrical conductor tracks 121. The supply container 117 according to the invention contains electrical contacts 122 in each chamber 118, for the conductor tracks 121 to make contact with the test elements 119 contained therein during electrochemical analysis of a sample on the test element. The test element 119, which is illustrated in FIG. 12 and projects partially out of the supply container 117, is slightly bent, so that the conductor tracks 121 arranged on it are pressed against the electrical contacts 122 on the supply container 117, thus making contact. However, contact may also be made when the test element 119 is inserted completely in the supply container 117. By way of example, in order to make contact, sprung contacts are also possible in the chambers 118. The supply container 117 (component 132 which makes electrical contact) may, for example, be a three-dimensional injection-molded circuit mount (MID).

Figure 13:
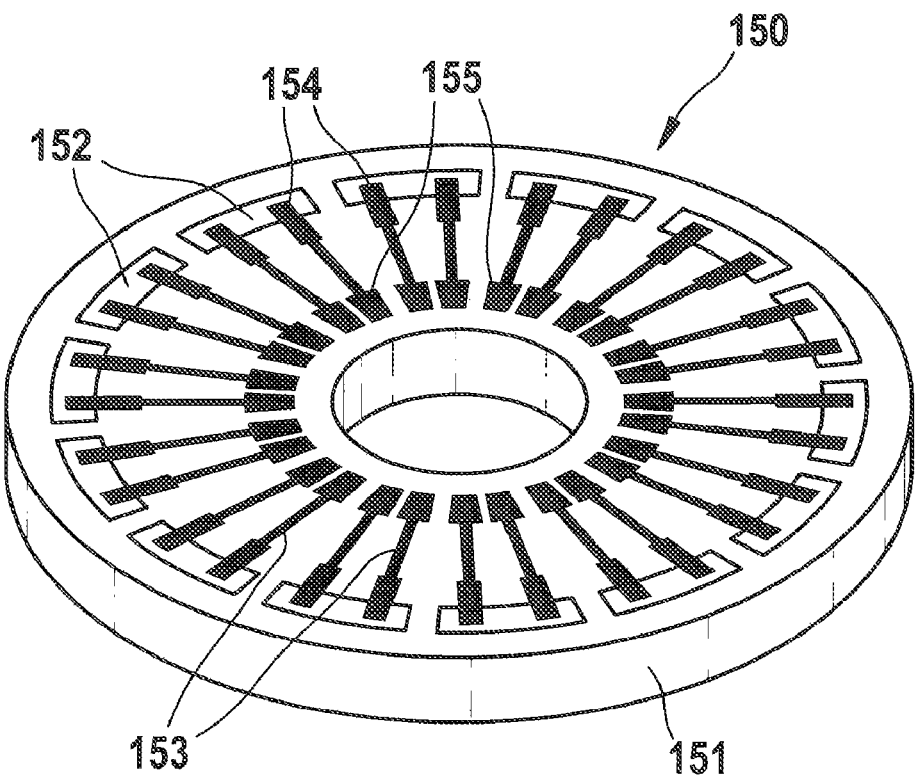
FIG. 13 illustrates a perspective view of a first embodiment of a test element according to the present invention, shown essentially in the form of an injection-molded circuit mount.

FIG. 13 shows a first embodiment of a test element according to the invention which is essentially in the form of an injection-molded circuit mount.

The test element 150 has a base body 151 composed of plastic. A multiplicity of test areas 152 for electrochemical analysis of a liquid sample are arranged on the base body 151. A dry chemical is located on the test areas 152 and reacts with the liquid sample. The test areas 152 are each connected on the test element 150 to electrical conductor tracks 153 which end at one end in an electrode structure 154 and at the other end in a contact structure 155. The electrode structure 154 in each case projects into a test area 152, and the contact structure 155 is used for connection to measurement electronics (which are not illustrated) for an analysis device. The base body 151 with the electrical conductor tracks 153, the electrode structure 154 and the contact structure 155 is an injection-molded circuit mount (MID). The test element 150 is in the form of a round disk on which the test areas 152 with associated conductor tracks 153 are arranged concentrically. This test element 150 can be rotated automatically or manually in an analysis device to a position in which electrical contact is made with a desired test area 152, and a sample provided thereon is analyzed electrochemically.

Figure 14:
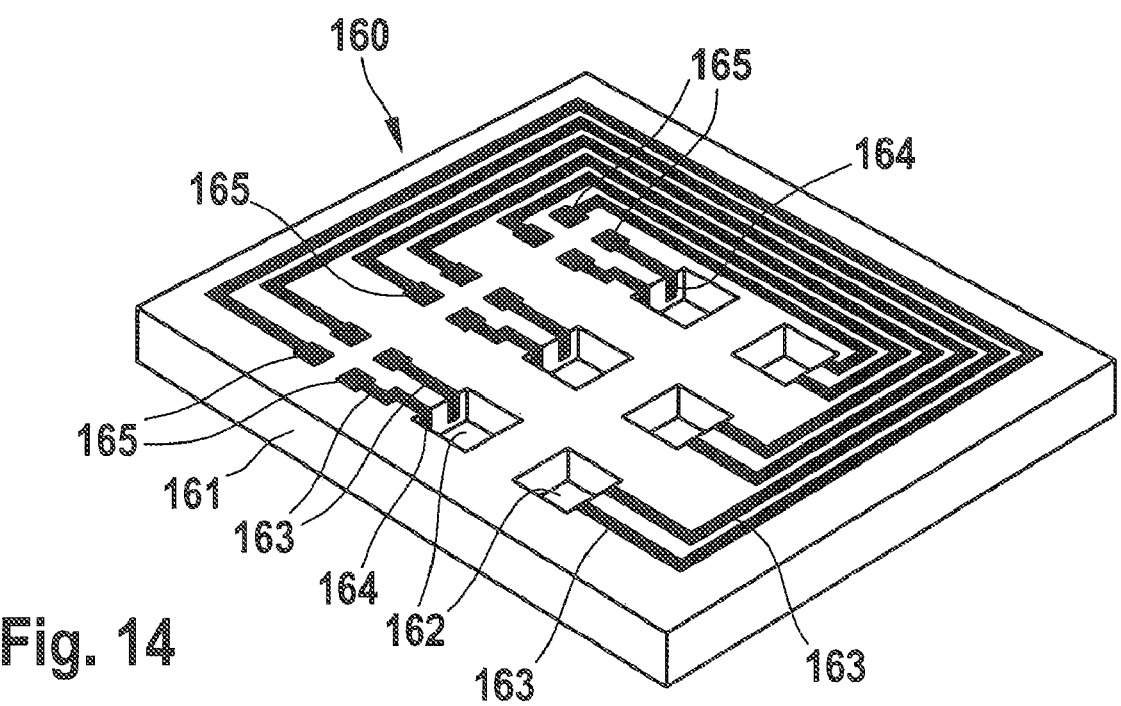
FIG. 14 illustrates a perspective view of a second embodiment of a test element according to the present invention, shown essentially in the form of an injection-molded circuit mount.

FIG. 14 shows a second embodiment of a test element according to the invention, which is essentially in the form of an injection-molded circuit mount.

The test element 160 has a base body 161 composed of plastic. Depressions 162 are formed in the base body 161 and can hold a sample to be analyzed and, possibly, an analysis means. Electrical conductor tracks 163 are provided for analysis of the sample and end at one end in an electrode structure 164 and at the other end in a contact structure 165. The electrode structure 164 in each case projects into a depression 162, and the contact structure 165 is used for connection to measurement electronics (which are not illustrated) for an analysis device. The base body 161 with the electrical conductor tracks 163, the electrode structure 164 and the contact structure 165 is an injection-molded circuit mount (MID). The test element 160 is in the form of a quadrilateral platelet. It contains six depressions 162. The electrical conductor tracks 163 are arranged on the test element 160 such that all the contact structures 165 are positioned in a restricted area on the test element 160. This makes it easier to position the test element 160 in order to make electrical contact with the samples, which are provided in different depressions, in an analysis device.

Injection-molded circuit mounts (Molded Interconnect Devices—MID) and methods for their production are known from the prior art, for example from DE 197 17 882 A1 or WO 00/67982 A1, the disclosures of which are hereby incorporated herein by reference in their entireties.

The expression MID technology covers various methods which can be used to produce three-dimensional electronic assemblies. The aim of these methods is integration of a circuit in a polymer (generally thermoplastic) mount component.

If conventional solutions for making electrical contact and for electronic circuits in devices are considered, spring contacts are frequently found which are plugged-in, adhesively bonded or hot-swaged in a housing (for example battery contacts in a large number of small devices). Another variant is metallic leaf springs or sliding contacts which make contact between the peripheral electrical components and a printed circuit board (for example sliding switches, push buttons or control wheels). The electronic circuit which controls the device operation is generally provided on a printed circuit board. The printed circuit board is fitted with the required electronic components. In very simple circuits, cables are soldered on or are connected to one another via plugs for wiring. All of these construction and connection techniques have the common feature that a plurality of components must be automatically or manually positioned, joined and mounted in order to construct a system which can operate. In this case, this results either in a considerable amount of hardware complexity for automated manufacture, or a considerable time penalty and labor cost for non-automated manufacture.

The use of MID technologies for production of components which make electrical contact in an analysis device in contrast offers the capability to reduce these disadvantages of conventional solutions, or to overcome them: assembly processes can be shortened or entirely avoided. The number of components is reduced and tolerance chains are shortened. Fewer different types of materials are used in the device, thus simplifying disposal and recycling. Some MID methods furthermore offer functions which are not possible with conventional solutions.

MID methods are based on selective application of electrically conductive metal layers on injection-molded plastic parts. A metallized polymer injection-molded part such as this may include electrical functions (for example the function of conductor tracks, plug contacts or sliding contacts) and mechanical functions (for example acting as an attachment element).

The most important MID methods which can be used to produce the injection-molded circuit mount for the analysis device according to the invention are two-component injection-molding, hot stamping, in-mold film coating, and laser structuring.

In two-component injecting-molding, a thermoplastic material component which can be metallized and a thermoplastic material component which cannot be metallized are sprayed onto one another in two process steps. In the final process, the work piece is in this case held in the mold on the surfaces which have been provided with their final contour during the first process. After injection-molding, the surface of the thermoplastic which can be metallized can be activated, and the desired metal layer thickness (for example copper layer thickness) is applied chemically or electrochemically. In the final step, a surface treatment is applied, for example nickel-gold. The material component which can be metallized has, for example, palladium admixed with it, which is used as a seed for the metallization. The palladium seeds are used, for example, as disintegration centers for stabilized nickel or copper solutions. Plastics which can inherently be metallized are used in other methods. A distinction is drawn in the metallization methods between chemical metallization with no external electrical power (without an electrical power source) and electrochemical metal deposition (with an electrical power source connected).

Components which can be metallized and may be used for the two-component injection-molding method are, for example, PES (polyethersulfone), PEI (polyetherimide), LCP (liquid-crystal polymer), PA (polyamide), PPA (polyphthalamide) or ABS (acrylonitrile butadiene styrene). Components which cannot be metallized are, for example, ABS+PSU (acrylonitrile butadiene styrene+polysulfone), PPA (polyphthalamide), PBT (polybutyleneterephthalate), PPS (polyphenylenesulfide), PES (polyethersulfone), PC (polycarbonate) or PA (polyamide).

In the case of hot stamping, the metallic structure (for example the conductor tracks) is applied in a process step after injection-molding by stamping out and stamping a metal sheet (for example a copper sheet) onto the plastic substrate. When using hot stamping, vias can be produced by filling holes with a conductive paste. In the case of hot stamping, the sheet must also be produced in addition to the single-component injection-molding of the substrate. Hot-stamping sheets for MID applications are generally characterized by a three-layer structure composed of a conductive copper sheet, an adhesive layer on the lower face and surface metallization which is used as an oxidation layer and to improve the capability for soldering and making contact. The copper sheets are electrolytically deposited on a copper sulfate solution, directly on a rotating titanium roller. The low shear strength of the copper sheet which is required to cut out the metallic structures (conductor tracks) in the stamping process is achieved by a specific method technique for sheet production, which leads to oriented crystal growth along the sheet surface. Copper sheets with layer thicknesses of about 12, 18, 35 and 100 μm are produced before application of different current loads, with the typical layer thickness that is frequently used for printed circuit board technology being about 35 μm. The adhesion strength of the sheet on the substrate is achieved either by means of an adhesive layer on the sheet lower face or by structuring of the sheet lower face. Possible materials which can be used for hot-stamping are, for example, ABS (acrylonitrile butadiene styrene), PA (polyamide), PBT (polybutyleneterephthalate), PC+ABS (polycarbonate+acrylonitrile butadiene styrene) and PPS (polyphenylenesulfide).

For in-mold film coating, the desired circuit is first of all structured on a plastic film. By way of example, the film may be structured using a subtractive flexible printed circuit technique, or additively by means of primer technology or hot-stamping processes. In flexible printed circuit technology, the polymer film (for example composed of polyamide) is metallized over its entire surface and is then structured using etching processes, subtractively. When using primer technology, printing methods are used to apply an adhesion promoter which can be metallized to the plastic film.

After structuring, the film can be shaped and can then be in-mold coated. The plastic part may be metallized before or after the in-mold film coating.

The in-mold coated plastic film may, for example, contain PEI (polyetherimide), PC (polycarbonate) or PC/PBT (polycarbonate/polybutyleneterephthalate). Materials which may be used for in-mold film coating of the film are, for example, PEI (polyetherimide), PC (polycarbonate), PBT (polybutyleneterephthalate), PET (polyethyleneterephthalate) or PEN (polyethylenenaphtenate).

One further possible method for production of the (three-dimensional) injection-molded circuit mount for the analysis device according to the invention is laser structuring.

In subtractive laser structuring, the injection-molded work piece is copper-plated, before structuring of the conductor tracks, over its entire area first wet-chemically and then electrolytically until the desired final layer thickness is achieved. An etching resist is then applied to the copper layer, for example a photoresist, in which energy introduced by means of UV radiation initiates a chemical reaction, or a galvanoresist, which is removed by means of laser beams. The resist is then structured by means of a laser beam, and the copper is then etched away in the structured areas. This is followed by surface treatment.

In additive laser structuring, thermoplastic materials are modified such that a metal-organic complex compound is dissolved or finely dispersed in the material. The conductor tracks to be produced on the thermoplastics that have been doped in this way are then specifically activated by means of a laser, and are then metallized in a chemical bath. Chemical copper electrolytes which typically produce copper layers with a thickness of about 5 to 8 μm are generally used for this process. A suitable surface finish can then be applied.

Laser structuring can for example, be applied to PEI (polyetherimide), PA (polyamide), LCP (liquid-crystal polymer), ABS (acrylonitrile butadiene styrene), PC (polycarbonate), PC+ABS (polycarbonate+acrylonitrile butadiene styrene), PBT (polybutyleneterephthalate), PI (polyimide) or PET (polyethyleneterephthalate), in which case the material may need to be doped.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An analysis device for analysis of a sample on a test element, comprising at least one first component configured to make electrical contact with at least one second component for electrical transmission therebetween, wherein the first component comprises an injection-molded circuit mount and further comprising a contact element for test element evaluation, the contact element comprising a contact surface having a plurality of contact ramps projecting over the contact surface and configured to make electrical contact with a test element which is positioned on the contact surface, the contact element further being configured to connect to a printed circuit board via conductor tracks provided on the contact element, wherein the contact element comprises the injection-molded circuit mount.

2. The analysis device of claim 1, wherein the electrical contact of the first component with the second component comprises a type of electrical contact selected from the group consisting of sprung contact, plug-in contact, solder contact, sliding contact and conductive-adhesive contact.

3. The analysis device of claim 1, wherein the first component comprises a functional assembly of the analysis device, and wherein the second component comprises the printed circuit board of the analysis device.

4. The analysis device of claim 3, wherein the functional assembly comprises a component selected from the group consisting of a barcode reader arrangement, a transport unit for test elements, a motor module, a measurement module, a positioning device for a test element magazine, a test element magazine holder which contains a sensor, and a heat-treatment device.

5. The analysis device of claim 1, wherein the second component comprises the test element and the test element is configured to be evaluated electrochemically.

6. The analysis device of claim 5, wherein the contact element for test element evaluation is integrated in a test element magazine.

7. A method for producing an analysis device for analysis of a sample on a test element, comprising:
producing at least one first component configured to make electrical contact with at least one second component for electrical transmission therebetween, the first component comprising a base body and a metallic conductor structure, said producing being performed according to a method for producing injection-molded circuit mounts, the analysis device further comprising a contact element for test element evaluation, the contact element comprising a contact surface having a plurality of contact ramps projecting over the contact surface and configured to make electrical contact with a test element which is positioned on the contact surface, the contact element further being configured to connect to a printed circuit board via conductor tracks provided on the contact element, wherein the contact element comprises the injection-molded circuit mount; and positioning and mounting the first component in the analysis device.

8. An analysis device for analysis of a sample on a test element, comprising at least one first component configured to make electrical contact with at least one second component for electrical transmission therebetween, wherein the first component comprises an injection-molded circuit mount and wherein the first component includes a positioning device configured for use with a rotatable test element magazine, the positioning device comprising a board for supplying electrical power and the second component includes a drive wheel, the drive wheel being driven by a motor, for driving the rotatable test element magazine, wherein the board comprises the injection-molded circuit mount having spring contacts, the drive wheel being configured as a segmented disk comprising a second injection-molded circuit mount with which electrical contact can be made.

9. A method for producing an analysis device for analysis of a sample on a test element, comprising:

producing at least one first component configured to make electrical contact with at least one second component for electrical transmission therebetween, the first component comprising a base body and a metallic conductor structure, said producing being performed according to a method for producing injection-molded circuit mounts, the analysis device further comprising a positioning device configured for use with a rotatable test element magazine, the positioning device comprising a board for supplying electrical power and a drive wheel, the drive wheel being driven by a motor, for driving the rotatable test element magazine, wherein the board comprises an injection-molded circuit mount having spring contacts, the drive wheel being configured as a segmented disk comprising the injection-molded circuit mount with which electrical contact can be made; and positioning and mounting the first component in the analysis device.

10. The method of claim 9, wherein the method for producing injection-molded circuit mounts comprises a method selected from the group consisting of two-component injection-molding, hot stamping, in-mold film coating and laser structuring.

11. An analysis device for analysis of a sample on a test element, comprising at least one first component configured to make electrical contact with at least one second component for electrical transmission therebetween, wherein the first component comprises an injection-molded circuit mount and further comprising a transport unit configured for use with one or more test elements, the transport unit comprising a push rod configured to transport a test element within the analysis device, the push rod having a guide bush configured to be guided in a guide device for transporting the test element, the guide bush having sprung contact lugs for making contact with a printed circuit board of the analysis device, the guide device having switching elements configured to press the contact lugs against the printed circuit board in specific positions of the guide bush in the guide device, wherein the guide bush comprises the injection-molded circuit mount.

12. A method for producing an analysis device for analysis of a sample on a test element, comprising:

producing at least one first component configured to make electrical contact with at least one second component for electrical transmission therebetween, the first component comprising a base body and a metallic conductor structure, said producing being performed according to a method for producing injection-molded circuit mounts, the analysis device further comprising a transport unit configured for use with one or more test elements, the transport unit comprising a push rod configured to transport a test element within the analysis device, the push rod having a guide bush configured to be guided in a guide device for transporting the test element, the guide bush having sprung contact lugs for making contact with a printed circuit board of the analysis device, the guide device having switching elements configured to press the contact lugs against the printed circuit board in specific positions of the guide bush in the guide device, wherein the guide bush comprises the injection-molded circuit mount; and positioning and mounting the first component in the analysis device.

13. An analysis device for analysis of a sample on a test element, comprising at least one first component configured to make electrical contact with at least one second component for electrical transmission therebetween, wherein the first component comprises an injection-molded circuit mount and further comprising a barcode reader arrangement comprising a housing section in which a barcode reader is arranged, wherein the housing section includes conductor tracks extending to the barcode reader, and further includes sprung contacts configured to make contact with a printed circuit board, the housing section with the conductor tracks and sprung contacts comprising the injection-molded circuit mount.

14. A method for producing an analysis device for analysis of a sample on a test element, comprising:

producing at least one first component configured to make electrical contact with at least one second component for electrical transmission therebetween, the first component comprising a base body and a metallic conductor structure, said producing being performed according to a method for producing injection-molded circuit mounts, the analysis device further comprising a barcode reader arrangement comprising a housing section in which a barcode reader is arranged, wherein the housing section includes conductor tracks extending to the barcode reader, and further includes sprung contacts configured to make contact with a printed circuit board, the housing section with the conductor tracks and sprung contacts comprising the injection-molded circuit mount; and positioning and mounting the first component in the analysis device.

15. An analysis device for analysis of a sample on a test element, comprising at least one first component configured to make electrical contact with at least one second component for electrical transmission therebetween, wherein the first component comprises an injection-molded circuit mount and further comprising a test element magazine holder which contains a sensor and electrical conductor tracks which run to the sensor, wherein the test element magazine holder with the conductor tracks comprises the injection-molded circuit mount.

16. A method for producing an analysis device for analysis of a sample on a test element, comprising:
produce at least one first component configured to make electrical contact with at least one second component for electrical transmission therebetween, the first component comprising a base body and a metallic conductor structure, said producing being performed according to a method for producing injection-molded circuit mounts, the analysis device further comprising a test element magazine holder which contains a sensor and electrical conductor tracks which run to the sensor, wherein the test element magazine holder with the conductor tracks comprises the injection-molded circuit mount; and
positioning and mounting the first component in the analysis device.

17. An analysis device for analysis of a sample on a test element, comprising at least one first component configured to make electrical contact with at least one second component for electrical transmission therebetween, wherein the first component comprises an injection-molded circuit mount and further comprising a measurement module configured to carry out a measurement on an analyte provided on a test element, the measurement module comprising a test element holder for holding the test element during the measurement, the test element holder including a heat-treatment device configured to provide heat-treatment of the test element, the heat treatment device comprising heating filaments and at least one sprung contact, wherein the test element holder comprises the injection-molded circuit mount.

18. A method for producing an analysis device for analysis of a sample on a test element, comprising:
producing at least one first component configured to make electrical contact with at least one second component for electrical transmission therebetween, the first component comprising a base body and a metallic conductor structure, said producing being performed according to a method for producing injection-molded circuit mounts, the analysis device further comprising a measurement module configured to carry out a measurement on an analyte provided on a test element, the measurement module comprising a test element holder for holding the test element during the measurement, the test element holder including a heat-treatment device configured to provide heat-treatment of the test element, the heat treatment device comprising heating filaments and at least one sprung contact, wherein the test element holder comprises the injection-molded circuit mount; and
positioning and mounting the first component in the analysis device.

19. An analysis device for analysis of a sample on a test element, comprising at least one first component configured to make electrical contact with at least one second component for electrical transmission therebetween, wherein the first component comprises an injection-molded circuit mount and further comprising a motor module which comprises a motor and a motor holder, the motor holder having contact lugs for making contact with a printed circuit board, wherein the motor holder with the contact lugs comprises the injection-molded circuit mount.

20. A method for producing an analysis device for analysis of a sample on a test element, comprising:
producing at least one first component configured to make electrical contact with at least one second component for electrical transmission therebetween, the first component comprising a base body and a metallic conductor structure, said producing being performed according to a method for producing injection-molded circuit mounts, the analysis device further comprising a motor module which comprises a motor and a motor holder, the motor holder having contact lugs for making contact with a printed circuit board, wherein the motor holder with the contact lugs comprises the injection-molded circuit mount; and
positioning and mounting the first component in the analysis device.

* * * * *